United States Patent [19]
Demonchaux et al.

[11] Patent Number: 5,474,988
[45] Date of Patent: Dec. 12, 1995

[54] 5-PHENYLPYRROLO-1,4-BENZOXAZINE AND 5-PHENYLPYRROLO-1,4-BENZOTHIAZINE COMPOUNDS, PROCESS AND INTERMEDIATES FOR THEIR PRODUCTION AND PHARMACEUTICAL COMPOSITIONS CONTAINING THEM

[75] Inventors: Patrice Demonchaux, Chalaronne; Patrick Lenoir, Romans, both of France

[73] Assignee: Kali-Chemie Pharma GmbH, Hanover, Germany

[21] Appl. No.: 196,462

[22] Filed: Feb. 15, 1994

[30] Foreign Application Priority Data

Feb. 17, 1993 [DE] Germany ............... 43 04 806.4

[51] Int. Cl.⁶ .................. C07D 265/34; C07D 279/14; A61K 31/535; A61K 31/54
[52] U.S. Cl. .................. 514/224.5; 514/230.2; 544/101; 544/32
[58] Field of Search ............... 514/224.5, 230.2; 544/101, 32

[56] References Cited

U.S. PATENT DOCUMENTS

| | | | |
|---|---|---|---|
| 4,985,420 | 1/1991 | Hamminga et al. | 514/224.5 |
| 5,010,076 | 4/1991 | Waldeck et al. | 514/221 |
| 5,198,437 | 3/1993 | Hamminga et al. | 514/224.5 |

FOREIGN PATENT DOCUMENTS

| | | |
|---|---|---|
| 529452 | 3/1993 | European Pat. Off. . |
| 2567126 | 1/1986 | France . |
| 90/07505 | 7/1990 | WIPO . |

OTHER PUBLICATIONS

Masuoka et al., "Syntheses of 3,4-Dihydro- . . . ", Chem. Pharm. Bull., vol. 34, No. 1, pp. 130-139 (1986).
Chemical Abstracts, vol. 103—87826r (1985) Abstract of Trapani et al., "Synthesis and antiinflammatory . . . ", Farmaco Ed. Sci., vol. 40, No. 5, pp. 369-376 (1985).

*Primary Examiner*—John M. Ford
*Attorney, Agent, or Firm*—Evenson, McKeown, Edwards & Lenahan

[57] ABSTRACT

Pharmacologically active compounds of formula I

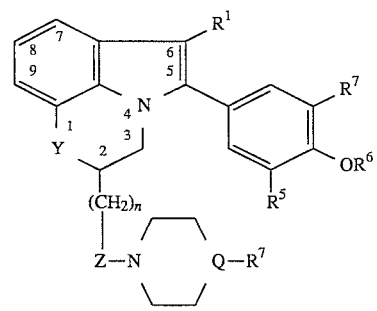

which can be substituted in the phenyl rings and in which
$R^1$ denotes hydrogen or lower alkyl,
$R^2$ denotes hydrogen or lower alkyl,
Y denotes oxygen or sulfur
n represents an integer from 1 to 3
Z represents a bond, a CO group or a CH= group,
Q denotes nitrogen or the CH group and
$R^7$, if Q denotes nitrogen, represents an optionally substituted pyridyl or phenyl radical or, if Q denotes the CH group, represents the N-methyl-N-(4-oxo-3H-pyrimidin-2-yl)amino group,
and their acid addition salts and processes and intermediates for their preparation.

10 Claims, No Drawings

5-PHENYLPYRROLO-1,4-BENZOXAZINE AND 5-PHENYLPYRROLO-1,4-BENZOTHIAZINE COMPOUNDS, PROCESS AND INTERMEDIATES FOR THEIR PRODUCTION AND PHARMACEUTICAL COMPOSITIONS CONTAINING THEM

BACKGROUND OF THE INVENTION

The present invention relates to novel 5-phenylpyrrolo-1,4-benzoxazine and -thiazine derivatives which carry a substituted piperazinoalkyl or piperidinoalkyl radical in the 2-position of the ring structure, and their salts and also pharmaceutical preparations containing these compounds and processes and intermediates for the preparation of these compounds.

Hamminga et al., U.S. Pat. Nos. 4,985,420 and 5,198,437 disclose esters and amides of 1,7-fused indole-2-carboxylic acid derivatives and cyclic alcohols or amines which are selective antagonists of neuronal 5-HT receptors and are suitable for the treatment of complaints induced by overstimulation of these receptors, for example in the gastrointestinal region.

Waldeck et al., U.S. Pat. No. 5,010,076 discloses amides of 1,7-fused indole-2-carboxylic acid derivatives with 3-amino-1,4-benzodiazepine derivatives. These compounds have cholecystokinin-antagonistic (cck-antagonistic) activity and an activity component which promotes gastric emptying.

SUMMARY OF THE INVENTION

It is the object of the present invention to provide novel pharmaceutically active compounds which can be used as antiallergic medicaments.

Another object of the invention is to provide novel derivatives of 1,7-fused indole compounds having useful pharmacological properties.

It has now been found that the novel 5-phenylpyrrolo-1,4-benzoxazine and -thiazine derivatives according to the invention have useful pharmacological properties and exhibit antiinflammatory and antiallergic activities and have a favorable activity profile with low toxicity and good tolerability. As a result of their activity profile, the substances according to the invention are suitable as antiinflammatory active compounds and antiallergics for the treatment of inflammatory or allergic disorders.

The present invention therefore relates to novel compounds of the general formula I See Formula I in which $R^1$ denotes hydrogen or lower alkyl, $R^2$ denotes hydrogen, halogen, lower alkyl, lower alkoxy, benzyloxy or hydroxyl, $R^3$ denotes hydrogen, halogen, lower alkyl, lower alkoxy or hydroxyl, $R^4$ denotes hydrogen, lower alkyl, lower alkoxy or hydroxyl, $R^5$ denotes hydrogen, lower alkyl, lower alkoxy or hydroxyl, $R^6$ denotes hydrogen or lower alkyl, Y denotes oxygen or sulfur, n represents a number from 1 to 3, Z represents a bond, the CO group or the $CH_2$ group, Q denotes nitrogen or the CH group and $R^7$, if Q denotes nitrogen, represents a pyridyl or phenyl radical which is optionally substituted by lower alkyl or halogen, or, if Q denotes the CH group, represents the N-methyl-N-(4-oxo-3H-pyrimidin- 2-yl)amino group, and their physiologically acceptable acid addition salts.

If, in the compounds of the formula I, the substituents denote or contain lower alkyl groups, these alkyl groups can be straight or branched and may contain in particular 1 to 4, preferably 1 to 2, carbon atoms and are preferably methyl. If the substituents denote halogen or contain halogen substituents, fluorine, chlorine or bromine, preferably fluorine or chlorine, are particularly suitable.

The substituent $R^1$ can denote hydrogen or lower alkyl and preferably represents lower alkyl, in particular methyl. The benzene ring of the tricyclic ring structure is preferably unsubstituted or monosubstituted in the 7- or 8-position. Suitable substituents are particularly lower alkoxy, preferably methoxy, hydroxyl or alternatively halogen, preferably chlorine or fluorine. The 5-phenyl substituent preferably carries a free hydroxy group in the 4-position. Accordingly, $R^6$ preferably represents hydrogen. If $R^6$ denotes lower alkyl, this is preferably methyl. The ring member Y is preferably oxygen.

The $(CH_2)_n$—Z chain is preferably a chain containing 2 to 3 carbon atoms, in particular the ethylene chain or a propylene or oxopropylene chain.

If the substituent $R^7$ is a pyridyl radical, this can be unsubstituted or substituted by lower alkyl or halogen. For example, pyridyl radicals which are substituted by lower alkyl, in particular methyl, or unsubstituted are suitable. A preferred group is a pyridin-2-yl group which can be optionally substituted. The 4-methylpyridin-2-yl radical proves to be particularly advantageous.

The compounds of the formula I contain an asymmetric carbon atom in the 2-position of the ring structure and can exist in several optically active enantiomeric forms or as racemates. The present invention includes both the racemic mixtures and the pure optical isomers of the compounds of the formula I.

According to the invention, the novel compounds of the formula I and their acid addition salts are obtained by a process in which a) for the preparation of compounds of the general formula Ia See Formula Ia in which $R^1$, $R^2$, $R^3$, $R^4$, $R^5$, $R^6$, n, Y, Q and $R^7$ have the above meaning and Z' represents a bond or the $CH_2$ group, compounds of the general formula IIa See Formula IIa in which $R^1$, $R^2$, $R^3$, $R^4$, $R^5$, $R^6$, n, Z' and Y have the above meaning, and X represents a leaving group which can be removed by aminolysis, are reacted with compounds of the general formula III See Formula III in which Q and $R^7$ have the above meaning, or b) for the preparation of compounds of the general formula Ib See Formula Ib in which $R^2, R^3, R^4, R^5, R^6, Y, n, Q$ and $R^7$ have the above meaning and $R^{1'}$ denotes lower alkyl, compounds of the general formula IVa See Formula IVa in which $R^{1'}, R^2, R^3, R^4, R^5, R^6, Y$ and n have the above meaning, are reacted with compounds of the formula III or c) for the preparation of compounds of the general formula Ic See Formula Ic in which $R^1, R^2, R^3, R^4, R^5, R^6, Y$ and n have the above meaning and $R^{7'}$ represents a pyridyl or phenyl radical which is optionally substituted by lower alkyl or halogen, compounds of the general formula Id See Formula Id in which $R^1, R^2, R^3, R^4, R^5, R^6, Y$, n and $R^{7'}$ have the above meaning, are reduced, or d) for the preparation of compounds of the general formula Ie See Formula Ie in which $R^2, R^3, R^4, R^5, R^6, Y, n, Z, Q$ and $R^7$ have the above meaning, the $COOR^5$ group is removed from compounds of the general formula V See Formula V in which $R^2, R^3, R^4, R^5, R^6, Y, n, Z, Q$ and $R^7$ have the above meaning and $R^8$ denotes lower alkyl, or e) for the preparation of compounds of the general formula If See Formula If in which $R^{1'}, R^2, R^3, R^4, R^5, R^6, Y, n, Z, Q$ and $R^{7'}$ have the above meaning, compounds of the general formula VI See Formula VI in which $R^2, R^3, Y, n, Z$ and $R^{7'}$ have the above meaning, are reacted with compounds of the general formula VIIa See Formula VIIa in which $R^{1'}, R^4, R^5,$ and $R^6$ have the above meaning, and, if desired, in the compounds of the formula I obtained, methoxy substituents $R^2, R^3, R^4, R^5$ and/or $OR^6$ are converted to hydroxyl and/or a benzyloxy substituent $R^2$ is converted to hydroxyl, and, if desired, the compounds of the formula I obtained are converted to their acid addition salts or the acid addition salts are converted to the free compounds of the formula I.

In the reactions described below, it is generally desirable to protect free phenolic hydroxy groups in the starting compounds during the reactions by means of readily removable protective groups and subsequently to remove these protective groups again. Protective groups which can be selected are protective groups known per se which can then be removed again by solvolysis or hydrogenolysis in a known manner. Suitable readily removable protective groups for phenolic OH groups are known, for example, from E. McOmie "Protective Groups in Organic Chemistry" Plenum Press 1971. Protective groups which can be selected, for example, for any phenolic hydroxy groups which may be present are ether protective groups known per se, for example lower alkyl groups or optionally substituted benzyl groups. Protective groups must of course be selected in each case taking into account the other radicals contained in the compound to be protected such that they can subsequently be removed easily under conditions under which other radicals contained in the molecule are not attacked.

The reaction of compounds of the formula IIa with compounds of the formula III according to process variant a) can be carried out by methods customary per se for the alkylation of amines. The reaction is advantageously carried out under basic conditions in an organic solvent which is inert under the reaction conditions.

Suitable radicals which can be removed by aminolysis in the compounds of the formula IIa are halogens such as chlorine, bromine or iodine or an acyloxy radical O—E, in which E is a lower alkanoyl radical or an organic sulfonic acid radical, for example the radical of a lower alkanesulfonic acid, such as, for example, methanesulfonic acid, or of aromatic sulfonic acids, such as benzenesulfonic acid or benzenesulfonic acids substituted by lower alkyl or by halogen such as bromobenzenesulfonic acid. For example, one particularly suitable radical is a toluenesulfonic acid radical. Suitable inert organic solvents include in particular aprotic solvents, preferably dimethylformamide and, for example, also aromatic hydrocarbons such as toluene, xylene or benzene, cyclic ethers such as dioxane, lower alkanols such as ethanol or mixtures of the abovementioned solvents. The reaction is advantageously carried out at elevated temperatures, for example temperatures between 50° and 120° C. The reaction is advantageously carried out with the addition of an amount of an organic or inorganic base sufficient for capturing the acid formed. However, an excess of the compound of the formula III can also be used and this can be utilized as an internal base. Examples of suitable organic bases are tertiary organic amines, in particular tertiary lower alkylamines such as triethylamine, tripropylamines, N-lower alkyl morpholines or N-lower alkylpiperazines. Suitable inorganic bases are, in particular, alkali metal carbonates or bicarbonates.

The reaction of acids of the formula IVa with amines of the formula III can be carried out by methods customary per se for the formation of amide groups by aminoacylation. Thus, the reaction of an amino compound of the formula III with an acid of the formula IVa can be advantageously carried out in the presence of a coupling reagent known from peptide chemistry as suitable for amide formation. Examples of coupling reagents which promote amide formation with the free acids by reacting with the acid in situ to form a reactive acid derivative include, in particular, carbonyldiimidazole or alkylcarbodiimides, for example cycloalkylcarbodiimides such as dicyclohexylcarbodiimide, and N-lower alkyl-2-halopyridinium salts, in particular halides or tosylates, for example N-methyl-2-chloropyridinium iodide (see, for example, Mukajama in Angew. Chemie 91 789 to 812), or alternatively lower alkyl chloroformates. The reaction in the presence of a coupling reagent can advantageously be carried out at temperatures from $-30°$ C. to $+50°$ C., preferably at approximately room temperature, in nonpolar, aprotic organic solvents such as halogenated hydrocarbons, for example dichloromethane and/or cyclic ethers such as tetrahydrofuran and/or aromatic solvents, if appropriate in the presence of an acid-binding amine. If desired, the acids of the formula IVa can also first be converted in a known manner into reactive acid derivatives, in particular acid halides, mixed acid anhydrides or esters and these then reacted in a known manner with the compounds of the formula III.

The reduction of amide compounds of the formula Id according to process variant c) can be carried out by methods customary per se for the reduction of amides. Suitable reductants are complex metal hydrides capable of amide reduction, in particular borane complexes, for example a borane/tetrahydrofuran complex in tetrahydrofuran, or alternatively aluminum hydrides such as lithium aluminum hydride or sodium bis(2-methoxyethoxy)aluminum hydride or lithium borohydride. The reaction takes place in a sufficiently anhydrous organic solvent which is inert under the reaction conditions. Suitable solvents are, for example, cyclic ethers such as tetrahydrofuran or dioxane or open-chain ethers such as diethyl ether, ethylene glycol dimethyl ether or diethylene glycol dimethyl ether, if appropriate in a mixture with aromatic hydrocarbons such as benzene or toluene. Depending on the type of reductant used, the reaction temperature can vary between 0° C. and the boiling temperature of the reaction mixture. For example, reduction using a borane/tetrahydrofuran complex in tetrahydrofuran at temperatures between room temperature and boiling temperature of the reaction mixture proves convenient.

The removal of the $COOR^8$ group from compounds of the general formula V according to process variant d) can be carried out in a known manner by first hydrolyzing the $COOR^8$ group under basic conditions and subsequently decarboxylating the hydrolysis product. The hydrolysis of the $COOR^8$ group is advantageously carried out by treating the compound of the formula V with an inorganic base, for example an alkali metal hydroxide, in a protic solvent, preferably a lower alcohol such as, for example, ethanol or an alcohol/water mixture. The reaction temperature for the hydrolysis can be between room temperature and the boiling point of the solvent. The acid obtained is then decarboxylated by heating to temperatures between 150° and 200° C. The decarboxylation can be carried out without a solvent or in a suitably high-boiling solvent. The reaction time can be between 1 and 12 hours. An amide group which may be present in the side chain in position 2 of the tricyclic ring structure is not attacked under the abovementioned conditions of basic hydrolysis and subsequent decarboxylation.

The reaction of the hydrazine compounds of the formula VI with the carbonyl compounds of the formula VIIa according to process variant e) can be carried out in a known manner by reacting the compounds with one another, for example under the conditions of a Fischer indole synthesis. The reaction can be carried out by heating to temperatures between 50° and 100° C. in acidic medium. For example, the reaction can be carried out in a water-miscible acid-containing organic solvent, for example an organic solvent such as a lower alcohol or acetic acid acidified with aqueous hydrochloric acid, hydrobromic acid, sulfuric acid or phosphoric acid or alternatively an organic acid, for example an organic sulfonic acid such as a toluenesulfonic acid. The reaction temperature can be between about 25° and 90° C.

In compounds of the formula I, in which the $R^6O$ group and/or the substituents $R^2$, $R^3$, $R^4$ and/or $R^5$ are methoxy, the methoxy groups can be cleaved in a known manner to give hydroxy groups using methods suitable for the cleavage of methoxyaryl ethers. For example, the ether cleavage can be carried out by treatment with boron tribromide in an oxygen-free organic solvent, in particular a halogenated hydrocarbon such as dichloromethane or a low-boiling aliphatic hydrocarbon such as n-pentane. The demethylation can also be carried out by treatment with other demethylating agents such as, for example, iodotrimethylsilane, Lewis acids, such as, for example, aluminum trichloride, or a boron trifluoride-dimethyl thioether complex in a halogenated hydrocarbon such as dichloromethane or chloroform. If desired, a benzyloxy group $R^2$ can be converted into a hydroxy group in a known manner, e.g. by catalytic hydrogenolysis.

The compounds of the formula I can be isolated from the reaction mixture and purified in a known manner. Acid addition salts can be converted into the free bases in a customary manner and the latter converted, if desired, into pharmacologically acceptable acid addition salts in a known manner.

Suitable pharmacologically acceptable acid addition salts of the compounds of the formula I are, for example, their salts with inorganic acids, for example hydrohalic acids, in particular hydrochloric acid, sulfuric acid or phosphoric acids, or with organic acids, for example lower aliphatic mono- or dicarboxylic acids such as maleic acid, fumaric acid, lactic acid, tartaric acid or acetic acid, or sulfonic acids, for example lower alkanesulfonic acid such as methanesulfonic acid or benzenesulfonic acids optionally substituted in the benzene ring by halogen or lower alkyl, such as p-toluenesulfonic acid, or cyclohexylaminosulfonic acid.

If in the synthesis of the compounds of the formula I racemates of the starting compounds of the formulae IIa, IVa, V or VI are employed, the compounds of the formula I are obtained in the form of racemates. Starting from optically active forms of the starting compounds, optically active compounds of the formula I can be obtained. The optically active compounds of the formula I can be obtained from the racemic mixtures in a known manner, for example by chromatographic separation on chiral separating materials or in the case of compounds of the formula I in which Z denotes a bond or the $CH_2$ group, by reaction with suitable optically active acids, for example tartaric acid, mandelic acid or 10-camphorsulfonic acid, and subsequent resolution into their optically active antipodes by fractional crystallization of the salts obtained. These can then be converted in turn into the free bases. If Z represents a CO group, it is advantageous for preparing optically active compounds of formula I to start from optically active intermediates. The optically active acid derivatives used as intermediates, for example the compounds of the formula IV, can be obtained in a known manner from the racemic mixtures of these acid derivatives through reaction with suitable optically active alcohols, for example menthol or 2 octanol, or optically active amines, for example 1-(1-naphthyl)ethylamine or 2-methylbenzylamine, preparing appropriate diastereoisomeric esters, amides or ammonium salts, separating these in a known manner by chromatography, and converting the enantiomers obtained into the free acids again.

The starting compounds of the formula II

See Formula II in which $R^2$, $R^3$, $R^4$, $R^5$, $R^6$, Y, n, Z' and X have the above meaning and $R^{1''}$ has the meaning indicated for $R^1$ or represents the lower alkoxycarbonyl group $COOR^8$, in which $R^8$ has the above meaning, are novel compounds which are useful intermediates for the preparation of pharmacologically active compounds, for example the compounds of the formula I.

The compounds of the formula II can be obtained in a known manner starting from the corresponding alcohols of the general formula VIII See Formula VIII in which $R^{1'''}$, $R^2$, $R^3$, $R^4$, $R^5$, $R^6$, Y, n and Z' have the above meaning, are obtained by converting the hydroxy group into a leaving group X in a known manner. Thus, for example to introduce a halogen radical X, the compounds of the formula VIII can be reacted with thionyl chloride or with phosphoric acid halides, for example phosphorus tribromide, in a known manner in a solvent which is inert under the reaction conditions, for example a halogenated hydrocarbon such as chloroform. Sulfonic acid radicals X can be introduced in a known manner by acylating compounds of the formula VIII with an appropriate sulfonyl chloride, preferably p-toluenesulfonyl chloride.

Alcohols of the formula VIII are novel compounds which are useful intermediates for the preparation of pharmacologically active compounds. Alcohols of the general formula VIIIa See Formula VIIIa in which $R^2$, $R^3$, $R^4$, $R^5$, $R^6$, Y, n and Z' have the above meaning and $R^{1'''}$ denotes lower alkyl or a $COOR^6$ group, can be obtained in a known manner by condensing hydrazine compounds of the general formula IX See Formula IX in which $R^2$, $R^3$, Y, n and Z' have the above meaning, with carbonyl compounds of the general formula VII See Formula VII in which $R^{1'''}$, $R^4$, $R^5$ and $R^6$ have the above meaning, in a known manner. The reaction of the compounds of the formula IX with the compounds of the formula VII can be carried out, for example, under the reaction conditions indicated above for process variant e) for the reaction of compounds of the formula VI with compounds of the formula VIIa.

For the preparation of compounds of the formula VIII in which $R^{1'''}$ denotes hydrogen, a $COOR^8$ group which may be present can be removed from compounds of the formula VIIIa in a known manner. Removal can be carried out, for example, in the manner described for the preparation of compounds of the formula Ie according to process variant d).

Alcohols of the general formula VIIIb

See Formula VIIIb in which $R^{1'}$, $R^2$, $R^3$, $R^4$, $R^5$, $R^6$, Y and n have the above meaning, can also be obtained starting from corresponding nitrile compounds of the general formula X See Formula X in which $R^{1'}$, $R^2$, $R^3$, $R^4$, $R^5$, $R^6$, Y and n have the above meaning, by converting the CN group into a $CH_2OH$ group in a known manner. To do this, the nitrile compounds of the formula X are first converted in a known manner by acidic solvolysis in a lower alcohol into corresponding esters of the general formula XXa See Formula XXa in which $R^{1'}$, $R^2$, $R^3$, $R^4$, $R^5$, $R^6$, Y and n have the above meaning and $R^9$ denotes lower alkyl. To do this, a solution of the compound of the formula X in a lower alcohol can be treated with acid, for example a hydrohalic acid, which is advantageously introduced into the solution as a hydrogen halide gas.

The resulting compounds of formula XXa can then be reduced in a knoll manner. Suitable reductants are, for example, hydride reductants capable of the reduction of esters to alcohols, for example the reductants indicated above under process variant c) for the reduction of compounds of the formula Id, in particular lithium aluminum hydride or sodium bis(2-methoxyethoxy) aluminum hydride. The reduction can be carried out according to customary methods, for example under the reaction conditions indicated for the reduction of compounds of the formula Id according to process variant c). In particular, reduction with lithium aluminum hydride in tetrahydrofuran proves expedient.

Compounds of the formula IX can be obtained in a known manner, starting from compounds of the general formula XI See Formula XI in which $R^2$, $R^3$, Y, n and Z' have the above meaning. To do this, the compounds of the formula XI are converted by treating with sodium nitrite in a known manner into the corresponding N-nitroso compounds of the general formula XII See Formula XII in which $R^2$, $R^3$, Y, n and Z' have the above meaning, and these are then reduced to the hydrazine compounds of the formula XI. For the reduction of the nitroso compounds of the formula XII, all reduction methods known per se for the reduction of nitroso compounds to corresponding hydrazine compounds can be employed. Suitable reductants are, for example, lithium aluminum hydride in tetrahydrofuran or metallic zinc powder in the presence of an acid or sodium dithionite. A catalytic hydrogenation of the nitroso compounds to the hydrazines of the formula IX is also possible. Compounds of the formula IX can also be obtained, starting from ester compounds of the general formula XIII See Formula XIII in which $R^2$, $R^3$, Y and $R^9$ have the above meaning and n' represents 0 to 3, by first reducing these in a known manner, by treating with sodium nitrite, into the corresponding N-nitroso compounds of the general formula XXX See Formula XXX in which $R^2$, $R^5$, Y, n' and $R^9$ have the above meaning, and then reducing these to the hydrazine compounds of the formula IX. For the reduction of the nitroso compounds of the formula XXX, reductants are employed which can reduce both the nitroso function and the carbonyl function. Lithium aluminum hydride, in particular, proves suitable. In the compounds of the formula XXX, first only the nitroso function can be reduced using a reductant which does not attack the carbonyl function, for example using metallic zinc powder in the presence of acid, and in the compounds thus obtained of the general formula XXI See Formula XXI in which $R^2$, $R^3$, Y, n' and $R^9$ have the above meaning, the carbonyl function subsequently reduced to the $CH_2OH$ group in a known manner, for example using lithium aluminum hydride.

Alcohols of the formula XI can be obtained by reducing ester compounds of the formula XIII in a known manner. The reduction can be carried out, for example, under the conditions indicated above for the reduction of the ester compounds of the formula XXa to the alcohols of the formula VIIIb.

Alcohol compounds of the general formula XIa

See Formula XIa in which $R^2$, $R^3$, Y and n have the above meaning, can also be obtained by reduction of compounds of the general formula XIV See Formula XIV in which $R^2$, $R^3$, Y, n and $R^9$ have the above meaning. The reduction can be carried out in a known manner using reductants suitable for the reduction of esters to corresponding alcohols. For example, the reduction can be carried out at elevated temperature, preferably boiling temperature of the reaction mixture, using lithium aluminum hydride in a cyclic ether such as tetrahydrofuran. Under these conditions, both the ester group and the oxo group of the ring structure are reduced.

Ester compounds of the general formula XIIIa

See Formula XIIIa in which $R^2$, $R^3$, Y, n and $R^9$ have the above meaning, can be obtained from compounds of the formula XIV by selective reduction of the oxo group of the ring structure. Suitable selective reductants are, for example, diborane or a boron hydride/tetrahydrofuran complex in tetrahydrofuran.

Compounds of the general formula XIIIb

See Formula XIIIb in which $R^2$, $R^3$, Y and $R^9$ have the above meaning, can be obtained starting from 2-aminophenols or -thiophenols of the general formula XV See Formula XV in which $R^2$, $R^3$, and Y have the above meaning, by reacting these with an alkyl 2,3-dibromopropionate of the general formula XVI See Formula XVI in which $R^9$ has the above meaning. The reaction can be carried out in a known manner in an organic solvent which is inert under the reaction conditions, for example dimethylformamide. The reaction is advantageously carried out with addition of an amount of a base, for example an inorganic base such as an alkali metal carbonate, which is sufficient for capturing the acid liberated. The reaction temperature can be between room temperature and 60° C.

Compounds of the formula XIV can be obtained starting from 2-nitrophenols or nitrothiophenols of the general formula XVII See Formula XVII in which $R^2$, $R^3$, and Y have the above meaning, by first reacting these with compounds of the general formula XVIII See Formula XVIII in which n and $R^9$ have the above meaning, to give compounds of the general formula XIX See Formula XIX in which $R^2$, $R^3$, Y, n and $R^9$ have the above meaning, and then cyclizing these under hydrogenating conditions. The reaction of the compounds of the formula XVII with the compounds of the formula XVIII can be carried out in a known manner under conditions customary for phenol ether formation. The subsequent cyclization of the compounds of the formula XIX can be carried out in a known manner under the conditions of a catalytic hydrogenation. Thus, the compounds can be treated with hydrogen in the presence of a hydrogenation catalyst in an organic solvent which is inert under the reaction conditions, preferably a lower alcohol. Suitable hydrogenation catalysts are palladium catalysts, in particular palladium/carbon, or alternatively platinum or rhodium catalysts. The latter prove expedient in the case in which the substituents $R_2$ and/or $R^3$ denote halogen.

Compounds of the general formula XIVa

See Formula XIVa in which $R^2$, $R^3$, Y and $R^9$ have the above meaning, can also be obtained starting from aminophenols or aminothiophenols of the formula XV by reacting these with maleic anhydride in a lower alcohol $R^9OH$. The reaction can be carried out in the presence of an organic base, for example a tertiary lower alkylamine, at elevated temperature, preferably boiling temperature of the reaction mixture.

The aminophenols and aminothiophenols of the formula XV are known or can be obtained in a known manner, for example by reduction of corresponding nitrophenols or nitrothiophenols of the formula XVII. The compounds of the formula XVII are known or can be obtained by nitration of known phenols or thiophenols in a known manner.

Compounds of the formula III are known or can be prepared by methods known per se or analogously to methods known per se.

Acids of the general formula IV

See Formula IV in which $R^{1'''}$, $R^2$, $R^3$, $R^4$, $R^5$, $R^6$, Y and n have the above meaning, and their acid derivatives are novel compounds, which are useful intermediates for the preparation of pharmacologically active compounds, for example the compounds of the formula I. The acids of the formula IV can be obtained in a known manner by hydrolysis of corresponding esters of the general formula XX See Formula XX in which $R^{1'''}$, $R^2$, $R^3$, $R^4$, $R^5$, $R^6$, Y, n and $R^9$ have the above meaning. If $R^{1'''}$ represents a $COOR^8$ group, the reaction conditions for the hydrolysis of the ester group $COOR^9$ in the side chain must be selected to be so mild that a simultaneous hydrolysis of the ring-bonded $COOR^8$ group is avoided.

Compounds of the formula XX can be obtained by reacting compounds of the general formula XXIa See Formula XXIa in which $R^2$, $R^3$, Y, n and $R^9$ have the above meaning, with compounds of the formula VII. The reaction can be carried out in a known manner, for example under the reaction conditions indicated in process variant e) for the reaction of compounds of the formula VI with compounds of the formula VIIa. Compounds of the formula XX in which $R^{1'''}$ denotes lower alkyl can also be obtained from corresponding nitriles of the formula X as described above.

Compounds of the formula V are novel compounds which are useful intermediates for the preparation of pharmacologically active compounds, for example the compounds of the formula I. They can be prepared by methods known per se.

Compounds of the general formula Va

See Formula Va in which $R^2$, $R^3$, $R^4$, $R^5$, $R^6$, Y, n, Z', Q, $R^7$ and $R^8$ have the above meaning, can be obtained by reacting compounds of the general formula IIb See Formula IIb in which $R^2$, $R^3$, $R^4$, $R^5$, $R^6$, Y, n Z', $R^8$ and X have the above meaning, with compounds of the formula III. The reaction can be carried out by methods customary per se for aminoalkylation, for example under the conditions indicated under process variant a) for the reaction of compounds of the formula IIa with compounds of the formula III.

Compounds of the general formula Vb

See Formula Vb in which $R^2$, $R^3$, $R^4$, $R^5$, $R^6$, Y, n, Q, $R^7$ and $R^8$ have the above meaning, can be obtained by reacting acids of the general formula IVb See Formula IVb in which $R^2$, $R^3$, $R^4$, $R^5$, $R^6$, Y, n and $R^8$ have the above meaning, with compounds of the formula III. The reaction can be carried out by methods customary for amide formation, for example under the conditions indicated under process variant b) for the reaction of compounds of the formula IVa with compounds of the formula III.

Compounds of the formula Va in which Z' represents a methylene group can also be obtained by reduction of corresponding compounds of the formula Vb with diborane or a boron hydride/tetrahydrofuran complex in tetrahydrofuran. Under these reaction conditions, the $COOR^6$ group is not attacked.

Compounds of the general formula Vc

See Formula Vc in which $R^2$, $R^3$, $R^4$, $R^5$, $R^6$, Y, n, Z, $R^{7'}$ and $R^8$ have the above meaning, can also be obtained by reacting compounds of the formula VI with compounds of the general formula VIIb See Formula VIIb in which $R^4$, $R^5$, $R^6$ and $R^8$ have the above meaning. The reaction can be carried out under the conditions indicated for the reaction of compounds of the formula VI with compounds of the formula VIIa according to process variant e).

Compounds of the formula VI are novel compounds which are useful intermediates for the preparation of pharmacologically active compounds. They can be prepared by methods known per se. For example, compounds of the formula VI can be obtained starting from compounds of the general formula XXII See Formula XXII in which $R^2$, $R^3$, Y, n, Z and $R^{7'}$ have the above meaning. To do this, the compounds of the formula XXII are converted into the corresponding N-nitroso compounds by treating with sodium nitrite in a known manner and the latter are then reduced to the hydrazine compounds of the formula VI. The formation of the nitroso compounds and their subsequent reduction can be carried out in a known manner under the conditions indicated above for the preparation of compounds of the formula IX starting from compounds of the formula XI and the preparation of compounds of the formula XXI can be carried out starting from compounds of formula XIII.

Compounds of the general formula XXIIa

See Formula XXIIa in which $R^2$, $R^3$, Y, n and $R^{7'}$ can have the above meaning, are obtained by reduction of compounds of the general formula XXIII See Formula XXIII in which $R^2$, $R^3$, Y, n and $R^{7'}$ have the above meaning and Z" denotes the $CH_2$ group or the CO group. The reduction can be carried out in a known manner using diborane or a boron hydride/tetrahydrofuran complex in tetrahydrofuran under the conditions indicated above for the reduction of compounds of the formula XIV to compounds of the formula XIIIa. In the reduction, a CO group Z" which may be present is likewise reduced.

Compounds of the formula XXIIb

See Formula XXIIb in which $R^2$, $R^3$, Y, n, Z' and $R^{7'}$ have the above meaning, can be obtained by reacting compounds of the general formula XXIV See Formula XXIV in which $R^2$, $R^3$, Y, n and Z' have the above meaning and X' represents halogen, preferably bromine, with compounds of the general formula IIIa See Formula IIIa in which $R^{7'}$ has the above meaning. The reaction can be carried out by methods customary per se for aminoalkylation and, for example, under the reaction conditions indicated for the reaction of compounds of the formula IIa with compounds of the formula III according to process variant a).

Compounds of the formula XXII in which Z denotes the CO group can be obtained by hydrolyzing esters of the formula XIIIa to corresponding acids and reacting these with compounds of the formula IIIa.

Compounds of the formula XXIII in which Z" denotes a ($CH_2$) group can be obtained by reacting compounds of the general formula XXV See Formula XXV in which $R^2$, $R^3$, Y, n and X' have the above meaning with compounds of the formula IIIa under conditions customary for aminoalkylation.

Compounds of the formula XXIII in which Z" denotes a CO group can be obtained by reacting acids obtained by hydrolysis of the esters of the formula XIV with compounds of the formula IIIa under conditions customary for aminoacylation, for example under the conditions described under process variant b).

Compounds of the formula XXV can be obtained by reacting aminophenols or aminothiophenols of the formula XV with compounds of the general formula XXVI See Formula XXVI in which $R^9$, n and X' have the above meaning. The reaction can be carried out in a known manner in an organic solvent which is inert under the reaction conditions, for example acetone. Advantageously, an inorganic base, for example an alkali metal carbonate, suitable for capturing the acid liberated is added and the reaction is carried out at elevated temperature, fox example boiling temperature of the reaction mixture.

Compounds of the formula XXIV can be obtained by reducing compounds of the formula XIII to the corresponding alcohols of the general formula XXVII See Formula XXVII in which $R^2$, $R^3$, n and Z' have the above meaning, and converting the hydroxy group in these into a halogen X' in a known manner. The reduction of the compounds of the formula XIII to the alcohols of the formula XXVII can be carried out, for example, under the reaction conditions indicated for the preparation of the alcohols of the formula VIIIb from compounds of the formula XXa. The introduction of a halogen radical X' can be carried out under the reaction conditions indicated for the preparation of compounds of the formula II from alcohols of the formula VIII.

Compounds of the formula VII are known or can be prepared by known methods or analogously to known methods, for example by reaction of compounds of the general formula XXIX See Formula XXIX in which $R^4$, $R^5$ and $R^6$ have the above meaning, with acid chlorides of the general formula XXVIII See Formula XXVIII in which $R^{1'''}$ has the above meaning.

If $R^6$ in the compounds of the formula XXIX denotes hydrogen, in the reaction with the acid chlorides of the formula XXVIII the corresponding phenol esters are first formed, which can then be converted into the compounds of the formula VII in a known manner under the conditions of a Fries rearrangement, e.g. by treating with aluminum trichloride in nitromethane.

The compounds of formula I and their pharmacologically acceptable acid addition salts are distinguished by interesting pharmacological properties and have antiinflammatory and antiallergic actions. In particular, the compounds show a favorable activity profile for the treatment of asthmatic complaints with low toxicity and good tolerability.

Asthma is a chronic inflammatory lung disease which is characterized by episodic reversible obstructions of the respiratory passages. It is generally assumed that the initiation of asthmatic symptoms and attacks stems from a parenchymal and interstitial cell type known as a mast cell. These mast cells contain preformed inflammatory mediators and spasmogens, in particular histamine. They are also capable of synthesizing de novo a variety of mediators derived from membrane lipids. Mast cells also act in conjunction with a multiplicity of accompanying cells which are all capable of synthesizing inflammatory and proinflammatory mediators.

As long as no allergy-inducing conditions are present, the mast cells are in a quasi-uninvolved waiting state. The key to allergic reactions lies in the binding of antigens to the membrane-bound IgE antibodies on mast cells. This binding crosslinks several IgE antibodies, which leads to activation of the mast cell. The mast cell as a result releases preformed mediators such as histamine and synthesizes new mediators such as leukotrienes.

Since asthma is an inflammatory obstructive lung disease, asthma therapy is essentially based on two approaches: alleviation of the symptoms by administering bronchodilators such as β-sympathicomimetics, xanthine derivatives and anticholinergics; administration of antiinflammatory active compounds such as disodium cromoglycate and steroids; and targeted therapy directed at specific mediators such as e.g. histamine. Treatment for alleviation of the symptoms is appropriate in about 50% of asthmatics, but does not contribute to alleviating the causes, i.e. the inflammation. Antiinflammatory active compounds may control the inflammation, but often have undesired side effects and are often administered simultaneously with bronchodilators. Targeted therapy directed at a specific mediator alone is completely inadequate, since there are a several mediators.

The compounds of the invention are characterized by antiinflammatory activity and act in a targeted manner against one or more of the three types of mediators, histamine, leukotrienes and blood platelet aggregation factor, which are involved not only in acute bronchospasms, but also in maintaining chronic inflammation, or are alternatively active against the target cells concerned via mediator-specific receptors. The compounds thus have a favorable activity profile, which is distinguished by a marked activity component directed against leukotrienes.

The antiinflammatory and antiallergic properties of the compounds can be demonstrated in vitro and in vivo in standard pharmacological test methods.

DESCRIPTION OF THE TEST METHODS

1. Determination of the inhibition of the anaphylactoid cutaneous reaction induced by histamine.

The inhibition of the anaphylactoid cutaneous reaction induced by histamine was determined in Sprague-Dawley rats having body weights of 150–180 g.

In order to determine the histamine-induced anaphylactoid skin reaction, 50 µl of a physiological saline solution containing 0.8 mg/ml of histamine were injected into the animals intradermally on one flank. Immediately afterward, a solution of 26.4 mg/kg of a blue dye (Evan's Blue) was administered i.v. to the animals.

The test substances were dissolved in distilled water which contains 1% by volume of dimethylformamide and 1% by volume of Tween®20 (=polyoxyethylene(20) sorbitan monolaurate). One hour before the histamine injection, each animal received $2 \times 10^{-5}$ mol/kg of test substance, in each case administered orally in 0.5 ml of solution. A control group received only the solvent for comparison.

The histamine-induced anaphylactoid reactions which manifested themselves by edema formation, swelling and exudation of blue dye are assessed 30 minutes after provocation by the histamine injection. This is carried out by visual determination of the extent of the exudation of blue dye at the sites of edema formation. With the aid of comparison scales, the percentage inhibition of the anaphylactoid reactions produced by the test substances is determined in comparison with the reactions of the control animals not treated with test substance.

The results obtained with compounds of the formula I by the above test method are reproduced in the following table A. The example numbers given as identifiers for the compounds of formula I refer to the subsequent preparative examples.

TABLE A

| Test substance Example No. | Inhibitory action against cutaneous histamine induced anaphylactoid reactions in rats % inhibition at a dose of $2 \times 10^{-5}$ mole/kg p.o. |
| --- | --- |
| 15 | 32 |
| 19 | 45 |
| 25 | 30 |
| 27 | 55 |
| 29 | 46 |
| 30 | 47 |
| 31 | 58 |
| 32 | 57 |
| 33 | 39 |
| 39 | 32 |
| 41 | 60 |
| 42 | 36 |
| 43 | 32 |
| 44 | 37 |

2. Determination of the minimum toxic dose.

Maximum doses of 300 mg/kg of the test substance were administered orally to male mice each weighing 20–25 g. The animals were carefully observed for symptoms of toxicity for 3 hours. All symptoms and deaths were additionally recorded over a period of 24 hours after administration. Associated symptoms were likewise observed and recorded. If death or severely toxic symptoms were observed, increasingly lower doses were administered to further mice. The lowest dose which caused death or severely toxic symptoms is indicated as the minimum toxic dose in the following Table B:

TABLE B

| Test substance Example No. | Minimum toxic dose mg/kg mice p.o. |
| --- | --- |
| 19 | >300 |
| 5 | >300 |

3. Determination of the anti-P.A.F. action in vitro.

P.A.F. (=Platelet Activating Factor=Platelet Aggregation Factor) is a phospholipid mediator which has a multiplicity of actions. The activation of blood platelet aggregation results in the induction of long-lasting bronchoconstrictions and hyperreactivity of the respiratory passages.

In this test, the effect of the test substances on platelet aggregation induced by addition of P.A.F. in a platelet suspension obtained from rabbit blood was investigated according to the method described by Mikashima et al. (Jap. J. Pharmacol. 44 (1987) 387–391).

A suspension of platelets obtained from rabbit blood was used which contains $4 \times 10^9$ platelets/ml in a modified Tyrode buffer solution (=Tyrode solution with the addition of 1.3 mM/l of $CaCl_2$ and 2.5 g/l of gelatine) adjusted to pH 7.4. Tyrode solution is an aqueous solution containing, per liter, 136.9 mmole of NaCl, 2.68 mmole of KCl, 2.31 mmole of $CaCl_2$, 1.0 mmole of $MgCl_2$, 11.9 mmole of $NaHCO_3$, 1.45 mmole of $NaH_2PO_4$ and 5.55 mmole of glucose. The platelets were concentrated from 10 ml blood samples of three rabbits (New Zealand hybrids, body weight 3–4 kg) in each case. To accomplish this, the blood samples were treated with ethylenediaminetetraacetic acid and washed according to the method of Artley et al. (Brit. J. Haematol. 19 (1970), 7– 17). A platelet-rich plasma was first separated by centrifugation (20 minutes at 400×g). The platelets were separated from the plasma by repeated centrifugation for 15 minutes at 1400×g. After the centrifugation, the blood platelets remaining in the sediment were resuspended in a Tyrode buffer solution (but without calcium). 0.4 mmole of lysine acetylsalicylate was then added, and the blood platelets were sedimented again after 15 minutes. The sediment was resuspended in the aforementioned modified Tyrode buffer solution, and the number of platelets in the suspension obtained was adjusted to the desired content.

A $40 \times 10^{-9}$ molar P.A.F. solution was employed as a reagent. This solution was prepared from a $1.8 \times 10^{-3}$ molar stock solution in chloroform. To do this, a 10 µl sample of the stock solution was evaporated to dryness and dissolved again in 180 µl of the modified Tyrode buffer solution, to which 0.25% of lipid-free bovine serum albumin had been added. $10^{-5}$ molar working solutions were then prepared from this and stored frozen. Samples of these solutions were appropriately diluted for tests.

In order to carry out the test, 50 µl of the blood platelet suspension and 10 µl of a $40 \times 10^{-5}$ molar solution of the compound to be investigated were added to 330 µl of the modified Tyrode buffer solution with stirring (1000 rpm) in an aggregation tube provided with a small magnetic stirrer. This corresponded to a final test substance concentration of $10^{-5}$ mole/l. After a preincubation time of 90 seconds, 10 µl of the P.A.F. preparation were added. For 4–5 minutes, the aggregation occurring in the aggregation tube was measured by means of a computerized aggregometer.

The aggregation occurring in the test tubes containing only the platelet suspension is rated as 0%. The aggregation occurring in the test tubes containing platelet suspension and P.A.F. preparation, in which a P.A.F.-induced increase in platelet aggregation takes place, is rated as 100%. The aggregation still occurring after addition of the test substances is measured, and from this the inhibition of the P.A.F.-induced increase in aggregation which takes place is calculated in %.

The results obtained with the compounds of formula I according to the above method are listed in the following Table C.

TABLE C

| Test substance Example No. | Anti-P.A.F. activity in vitro. % inhibition of the P.A.F.-induced aggregation of blood platelets from rabbit blood at a test substance concentration of $10^{-5}$ mole/liter |
| --- | --- |
| 1 | 80 |
| 2 | 97 |
| 3 | 92 |
| 4 | 99 |
| 5 | 100 |
| 6 | 100 |
| 9 | 67 |
| 12 | 93 |
| 13 | 94 |
| 14 | 100 |
| 15 | 100 |
| 17 | 99 |
| 18 | 78 |
| 19 | 71 |
| 20 | 92 |
| 22 | 84 |
| 23 | 66 |
| 25 | 91 |
| 26 | 82 |
| 28 | 83 |
| 29 | 50 |

TABLE C-continued

| Test substance Example No. | Anti-P.A.F. activity in vitro. % inhibition of the P.A.F.-induced aggregation of blood platelets from rabbit blood at a test substance concentration of $10^{-5}$ mole/liter |
|---|---|
| 30 | 69 |
| 31 | 52 |
| 32 | 79 |
| 33 | 43 |
| 34 | 77 |
| 37 | 48 |
| 42 | 40 |
| 43 | 95 |
| 44 | 99 |
| 48 | 69 |
| 51 | 65 |
| 54 | 65 |
| 63 | 80 |
| 65 | 52 |
| 67 | 97 |
| 68 | 96 |
| 69 | 97 |
| 70 | 93 |
| 71 | 84 |
| 72 | 79 |

4. In vitro determination of 5-lipoxygenase inhibition.
4a. In vitro determination of inhibition of 5-lipoxygenase activity in polymorphonuclear rat leucocytes.

Arachidonic acid contained in cell membranes is released after activiation of the polymorphonuclear leucocytes (=PMN). During the course of this, under the action of the enzyme 5-lipoxygenase (=5-LO) arachidonic acid metabolites are synthesized which can be converted to leucotriene $B_4$ (=$LTB_4$) by $LTA_4$ hydrolase. $LTB_4$ is a principal metabolite of the arachidonic acid metabolism taking place on activation of the enzyme 5-LO by the inflammatory stimulus in the cell membrane. In in vitro systems, this metabolite is secreted from PMNs. In order to investigate the 5-lipoxygenase-inhibiting properties, the inhibitory activity of the test substances is determined in vitro on the biosynthesis of the arachidonic acid derivative leucotriene $B_4$ (=$LTB_4$) in rat peritoneal PMNs. To accomplish this, the content of $LTB_4$ in a culture medium of rat peritoneal PMNs was determined after stimulation by calcimycin (=calcium-ionophore A23187) such as described by J. Gillard et al., Can. J. Physiol. Pharmacol. 67 (1989), 17.

A cell suspension containing peritoneal PMNs of male Sprague-Dawley rats (body weight 200 to 250 g) was obtained in a known manner as follows: 6 ml of a solution containing 27.9 g/l of sodium thioglycolate were injected i.p. into the animals in order to induce the PMN invasion due to this inflammatory stimulus. After 22 hours, the animals were sacrificed by means of lethal ether anaesthesia. 20 ml of a Hank's salt solution (=Hank's Balanced Salt Solution= HBSS), but without $Ca^{++}$ and $Mg^{++}$ ions and with 0.2% by weight of sodium citrate, were then injected into the abdominal cavity. The suspension of accumulated cells was removed from the abdominal cavity and the cells were separated by centrifugation (10 minutes at 400×g). The cells were purified by repeated centrifugation in the presence of Ficoll-Paque®, (=metrizoic acid preparation, d=1077, manufacturer Pharmacia), then washed twice with HBSS containing $Ca^{++}$ and $Mg^{++}$ ions and resuspended in HBSS containing $Ca^{++}$ and $Mg^{++}$ ions and buffered with 10 mM HEPES (= hydroxyethylpiperazinoethanesulfonic acid).

In order to carry out the tests, samples of 0.7 ml of the PMN suspension (=$0.5 \times 10^6$ cells) in each case were incubated for 15 minutes at 22° C. in plastic tubes containing 10 µM of the test substance in dimethylformamide or, as a control experiment, only containing dimethylformamide. The $LTB_4$ synthesis was initiated in the samples by addition of calcimycin (final concentration 5 µm), and the samples were incubated for 10 minutes at 22° C. Only solvent was added to blank control samples. After 10 minutes, the reaction was terminated by addition of 0.3 ml of cold methanol. The samples were kept for 1 hour at 4° C. and then centrifuged (5 minutes at 10,000×g). The supernatant liquid was investigated to determine its $LTB_4$ content by means of reverse phase high-pressure liquid chromatography (=reverse phase HPLC). To do this, a 5 µM-C18 silanized silica gel column (Hichrom® $ODS_2$, 250×4.6 mm) was used as an adsorbent and a mixture of methanol/water/acetic acid 72:28:0.02 v/v/v adjusted to pH 5.7 with ammonia having a flow rate of 1 ml/min was used as an eluent. The $LTB_4$ was identified by comparison with authentic standard solutions eluting at the same time and determined at a wavelength of 270 nm. The $LTB_4$ contents are determined from comparison with calibrated standard solutions, and from this the inhibitory activity of the test substances was calculated in % inhibition of the $LTB_4$ synthesis in comparison with the control samples containing no test substance. The results obtained using this test method are listed in the following Table D.

TABLE D

| Test Substance Example No. | In vitro & inhibitory activity on $LTB_4$ formation in rat PMNs stimulated by calcium ionophore A23187 at a test substance concentration of $10^{-5}$ mole/l |
|---|---|
| 2 | 89 |
| 3 | 96 |
| 4 | 100 |
| 9 | 86 |
| 12 | 100 |
| 13 | 98 |
| 14 | 90 |
| 15 | 94 |
| 16 | 60 |
| 19 | 45 |
| 20 | 75 |
| 21 | 42 |
| 23 | 92 |
| 24 | 73 |
| 26 | 67 |
| 27 | 90 |
| 28 | 48 |
| 30 | 100 |
| 31 | 81 |
| 32 | 98 |
| 33 | 90 |
| 34 | 95 |
| 35 | 79 |
| 36 | 89 |
| 37 | 100 |
| 38 | 97 |
| 39 | 98 |
| 40 | 82 |
| 41 | 84 |
| 43 | 66 |
| 44 | 100 |
| 49 | 88 |
| 52 | 53 |
| 55 | 63 |
| 56 | 76 |
| 57 | 85 |
| 58 | 54 |
| 62 | 56 |
| 65 | 64 |
| 67 | 100 |
| 68 | 90 |
| 69 | 100 |
| 70 | 68 |

TABLE D-continued

| Test Substance Example No. | In vitro & inhibitory activity on LTB$_4$ formation in rat PMNs stimulated by calcium ionophore A23187 at a test substance concentration of $10^{-5}$ mole/l |
|---|---|
| 71 | 100 |
| 72 | 100 |
| 73 | 100 |
| 74 | 100 |
| 75 | 51 |

4b. In vitro determination of inhibitory activity on 5-lipoxygenase concentrated from peritoneal PMNs of the guinea-pig.

An inhibition of 5-lipoxygenase can be caused by direct inhibitory action of the substances on the enzyme and/or by interference with the activation of the enzyme. While in test 4a the 5-lipoxygenase inhibition of the substances was investigated in rat PMN cells, in test 4b the inhibitory activity of the substances was investigated on free 5-LO concentrated from guinea-pig PMN cells according to the method of D. Aharony et al., J. Biol. Chem. 261 (1986), 11512–11519 (1986).

The 5-LO was concentrated in a known manner from PMNs of male Dunkin-Hartley guinea-pigs (body weight 400 to 500 g) as follows. 10 ml of a solution containing 27.9 g/l of sodium thioglycolate were injected i.p. into the animals in order to induce the PMN invasion as a result of this inflammatory stimulus. After 22 hours, the animals were sacrificed by lethal ether anaesthesia. 70 ml of HBSS without $Ca^{++}$ and $Mg^{++}$ ions and containing 0.2% by weight of sodium citrate were then injected into the abdominal cavity. The cell suspension (>80% of the cells are PMNs) was withdrawn from the abdominal cavity, filtered through a cheese-making filter cloth, and washed twice with a 50 mM potassium phosphate buffer solution of pH 7.4, which contained 0.5 mM ethylenediaminetetraacetic acid, 1% by weight of gelatine and 20 µM indomethacin. The cells were resuspended, and the PMN suspension containing $10^8$ cells/ml was homogenized three times for 15 seconds each in an ice-bath in a homogenizer of the Labsonic™ type set at high speed. The resulting suspension was centrifuged at 4° C. (15 minutes at 10,000×g). The supernatant liquid was used for the investigation as a solution of the free 5-LO enzyme.

The experiments were carried out at 37° C. for 7 minutes using 0.625 ml samples of this enzyme solution. For the experiments, the enzyme solution (=equivalent of 2.5×$10^7$ cells), 0.5 mM glutathione, 1 mM ATP and 0.3 mM calcium chloride were added to test tubes. 10 µmole of the test substance were added to the samples dissolved in sufficient dimethylformamide such that the dimethylformamide concentration in each test tube is 0.5%. Only dimethylformamide was added to the control samples. After 2 minutes, the formation of 5-(S)-hydroxy-6,8,11,14-eicosatetraenoic acid (=5-METE) was initiated by addition 10 µM arachidonic acid. After 5 minutes, the reaction was terminated by addition of 0.625 ml of a mixture of methyl acetate/methanol/0.2 m citric acid 15:2:0.5 v/v/v. 5-HETE was extracted twice using this solvent mixture. The 5-HETE-containing phases were combined and evaporated to dryness under a nitrogen atmosphere. The residue was taken up in a mixture of methanol/water/acetic acid 75:21:0.02 v/v/v having a pH of 5.7, and the solution was investigated for its content of 5-HETE by means of reverse phase HPLC. To accomplish this, a 5 µM-C18 silanized silica gel column (Hichrom® ODS$_2$, 250×4.6 mm) was employed as the adsorbent and a mixture of methanol/water/acetic acid 75:21:0.02 adjusted to pH 5.7 with ammonia and having a flow rate of 1 ml/min was used as the eluent. 5-HETE, which was eluted as a single peak after 20 minutes, was identified by comparison with standard solutions eluted at the same time and determined using a UV light detector at a wavelength of 235 nm. Quantitative determination was carried out by comparison of the peak area obtained with peak areas occurring in the calibrated standard solutions. From the 5-HETE contents of the samples determined, the inhibitory activity of the test substances was calculated in % inhibition of 5-HETE synthesis in comparison to the control samples containing no test substance.

The results obtained with this experimental method are listed in the following Table E.

TABLE E

| Test Substance Example No. | In vitro % inhibitory activity on 5-HETE formation caused by free 5-LO at a test substance concentration of $10^{-5}$ mole/liter |
|---|---|
| 3 | 53 |
| 4 | 100 |
| 9 | 88 |
| 12 | 100 |
| 11 | 95 |
| 13 | 99 |
| 15 | 94 |
| 16 | 57 |
| 17 | 100 |
| 18 | 100 |
| 10 | 46 |
| 20 | 100 |
| 21 | 30 |
| 22 | 97 |
| 23 | 93 |
| 25 | 92 |
| 26 | 96 |
| 27 | 50 |
| 28 | 44 |
| 29 | 67 |
| 34 | 97 |
| 35 | 55 |
| 36 | 65 |
| 38 | 100 |
| 39 | 100 |
| 40 | 56 |
| 42 | 55 |
| 43 | 77 |
| 44 | 98 |
| 49 | 99 |
| 54 | 63 |
| 59 | 70 |
| 64 | 74 |
| 62 | 77 |
| 65 | 99 |
| 67 | 100 |
| 69 | 100 |
| 71 | 100 |
| 72 | 100 |
| 73 | 100 |
| 74 | 100 |
| 75 | 100 |

4c. In vitro determination of 5-lipoxygenase inhibition in human blood.

The inhibitory activity of the test substances on the 5-LO activity in human whole blood taking place after stimulation by calcimycin is investigated according to the method described by P. Gresele et al. (Biochem. Biophys. Commun. 137 (1986), 334).

For carrying out the test, human blood is collected in sterile 50 ml test tubes which contain 10 units of heparin/ml of blood and incubated for 5–10 minutes at 37° C. Amounts of test substance, dissolved in 10 µl of dimethylformamide, are added to 2 ml samples of this blood such that a final concentration of test substance of 10 µmol/l is achieved in the samples. Only 10 μl of the solvent were added to control samples. The samples were then incubated for 10 minutes at 37° C. In order to stimulate LTB$_4$ synthesis, an amount of calcimycin, dissolved in 200 μl of plasma, was added to the samples such that a calcimycin concentration of 60 μmol/l was achieved, and the samples were incubated for a further 30 minutes at 37° C. The reaction was then terminated by addition of 200 μl of an ethylene glycol tetraacetate solution (corresponding to an ethylene glycol acetate concentration in the sample of 100 mmol/l). The samples are kept in an ice-bath for 10 minutes and then centrifuged (5 minutes at 1000×g). The supernatant liquids, which contain the LTB$_4$ formed during the reaction time, are each separated and, for precipitation of the proteins contained therein, mixed with 3 ml of acetone and kept for 45 minutes at 4° C. Then the samples are centrifuged again (5 minutes at 1500×g), the supernatant liquids are separated, and the content of LTB$_4$ therein is determined in a known manner by means of an enzyme immunoassay (=EIA). From the measured LTB$_4$ values, the inhibitory activity of the test substances in human whole blood was calculated in % inhibition of LTB$_4$ synthesis in comparison to the control samples containing no test substance. The results obtained using this test method are listed in the following Table F.

TABLE F

| Test Substance Example No. | In vitro % inhibitory activity on LTB$_4$ formation in human blood stimulated by calcimycin at a test substance concentration of $10^{-5}$ mole/liter |
|---|---|
| 4 | 86 |
| 41 | 100 |
| 67 | 100 |
| 69 | 95 |
| 71 | 100 |
| 72 | 95 |
| 73 | 100 |
| 74 | 100 |
| 75 | 96 |

Due to their activities described above, the compounds of formula I are suitable as anti-inflammatory and antiallergic medicaments for larger mammals, in particular humans, for treating inflammatory and allergic disorders. The orally active compounds according to the invention can act in several ways, as they are active against several of the principle mediators which are involved in inflammatory processes and asthmatic complaints.

Because of this activity profile, it is to be expected that in the treatment of allergy-related and non-allergy-related asthmatic complaints, the compounds according to the invention not only alleviate the symptoms associated with asthmatic disorders, but can also reduce the inflammation associated therewith. The doses to be used may differ in individual cases and of course vary depending on the nature of the condition to be treated, the substance used and the form of administration. For example, parenteral formulations generally contain less active compounds than oral preparations. In general, however, pharmaceutical formulations having an active compound content of 10 to 250 mg per individual dose are suitable for administration to larger mammals, in particular humans.

As medicines, the compounds of formula I can be contained in pharmaceutical preparations, such as e.g. tablets, capsules, suppositories and solutions, with customary pharmaceutical auxiliaries. These pharmaceutical preparations can be prepared by known methods using conventional solid excipients such as e.g. lactose, starch or talc or liquid paraffins and using conventional pharmaceutical adjuvants, for example tablet disintegrants, solubilizers or preservatives.

The following examples are intended to illustrate the invention in further detail without restricting its scope.

The structures of the novel compounds were confirmed by spectroscopic investigations, particularly by analysis of the IR and NMR spectra, and also by elemental analysis. The purity of the intermediates was monitored by thin-layer chromatography.

EXAMPLE 1

2,3-Dihydro-5-(4-methoxyphenyl)-6-methyl-2-[2-(4-(4methylpyridin-2-yl)piperazin-1-yl)ethyl] pyrrolo[1,2,3-de] -1,4-benzoxazine A) A mixture of 76.4 g of 2-aminophenol and 68.6 g of maleic anhydride in 1 liter of methanol was stirred at room temperature. After addition of 100 ml of triethylamine, the yellow mass dissolved and the solution was heated for 7 hours at reflux temperature. The methanol was then removed by evaporation under reduced pressure, and the remaining oil was added to ice-water. The mixture was extracted with dichloromethane, and the organic extract was dried over sodium sulfate and evaporated. The remaining residue was crystallized from ethanol. In this way, 47.5 g of methyl (3-oxo-2,3-dihydro-4H-1,4-benzoxazin-2-yl)acetate were obtained as white crystals having a melting point of 140° C.

B) 12 g of lithium aluminum hydride were slowly poured into 300 ml of tetrahydrofuran with cooling at 0° C. A solution of 18 g of the ester obtained above in 200 ml of tetrahydrofuran was then added dropwise. The reaction mixture was subsequently heated under reflux for 2 hours. To work-up the mixture, 12 ml of water and subsequently 100 ml of tetrahydrofuran, 12 ml of 4N sodium hydroxide solution and again 30 ml of water were slowly added. The solution was filtered, and the residue was washed with diethyl ether. The filtrate was concentrated and the residue which remained was dissolved in dichloromethane. The solution was dried over sodium sulfate and filtered, and the solvent was evaporated. 14.1 g of 4H-2,3-dihydro-2-(2-hydroxyethyl)- 1,4-benzoxazine were obtained as an oil.

C) 12 g of the alcohol obtained above were poured into a mixture of 100 ml of water, 50 g of ice and 10 ml of 12N hydrochloric acid solution. A solution of 4.3 g of sodium nitrite in 10 ml of water was added dropwise to the solution with cooling to 0° to 5° C. After the addition was completed, the temperature of the reaction mixture rose to 20° C. The paste obtained was extracted with toluene, and the organic extract was dried over sodium sulfate and concentrated. 14.6 g of 2,3-dihydro- 2-(2-hydroxyethyl)-4-nitroso-1,4-benzoxazine were obtained as an oil.

D) 21 g of the nitroso compound obtained above were slowly poured into 100 ml of tetrahydrofuran containing 8 g of lithium aluminum hydride. The reaction mixture was stirred at room temperature for half an hour and then cooled to −10° C. To work-up the mixture, 8 ml of water, 10 ml of tetrahydrofuran and 15 ml of 10% strength sodium hydroxide solution were added successively. The solution was filtered, and the residue was washed with dichloromethane. The filtrate was dried over sodium sulfate and concentrated. 17.3 g of 4-amino-2,3-dihydro-2-(2-hydroxyethyl)-1,4-benzoxazine were obtained as a yellow oil.

E) 17.3 g of the hydrazine compound obtained above and 16.1 g of 4-methoxypropiophenone were dissolved in 60 ml of ethanol. The reaction mixture was heated under reflux for 2.5 hours under a nitrogen atmosphere. 12 ml of 12N hydrochloric acid solution were then added dropwise at reflux temperature, distributed over a period of half an hour. The reaction mixture was then cooled. For work-up, 100 ml of water were added and the mixture was extracted with dichloromethane. The dichloromethane extract was dried over sodium sulfate and concentrated. 16 g of 2,3,-dihydro-2-(2-hydroxyethyl)- 5-(4-methoxyphenyl)-6-methylpyrrolo[ 1,2,3-de]-1,4-benzoxazine were obtained as an oil.

F) 25 g of tosyl chloride were added to a solution, cooled to about 0° C., of 34 g of the alcohol obtained above in 80 ml of pyridine. The reaction mixture was then heated for 5 hours at 60° C. For work-up, the reaction mixture was poured into water and extracted with dichloromethane. The extract was dried over sodium sulfate and concentrated. 47.5 g of 2,3-dihydro-2-[ 2-(p-toluenesulfonyloxy-)ethyl]-5-(4-methoxyphenyl)-6-methylpyrrolo[ 1,2,3-de]-1,4-benzoxazine were obtained as an oil.

G) A mixture of 15.5 g of the tosyl compound obtained above and 6 g of 1-(4-methylpyridin-2-yl)piperazine were heated for 6 hours at 90° C. in 5 ml of dimethyformamide. For work-up, the reaction mixture was then poured into 50 ml of water. The title compound was extracted from the mixture with dichloromethane and purified by column chromatography using ethyl acetate/cyclohexane 1:1 and then crystallized from ethanol. 2.3 g of the title compound were obtained as a white powder having a melting point of 165° C.

EXAMPLE 2

2,3-Dihydro-5-(4-hydroxyphenyl)-6-methyl-2-[2-(4-(4-methylpyridin-2-yl)piperazin-1-yl)ethyl] pyrrolo[1,2,3-de] -1,4-benzoxazine 1.9 g of 2,3-dihydro-5-(4-methoxyphenyl)-6-methyl-2-[2-( 4-(4-methylpyridin-2-yl)piperazin-1-yl)ethyl]pyrrolo[1,2,3-de] -1,4-benzoxazine (Preparation see Example 1) were dissolved in 5 ml of anhydrous dichloromethane under a nitrogen atmosphere. The solution was cooled to 0° to 5° C. and 1.5 g of boron tribromide were then added all at once. The reaction mixture was subsequently stirred for 3 hours at room temperature. The reaction mixture was then again cooled to 0° to 5° C. and 10 ml of methanol were added, and the reaction mixture was again stirred for half an hour at room temperature and then evaporated. The residue was dissolved in 20 ml of aqueous ammonia solution (pH=8/9) and the solution was extracted with dichloromethane. The extracts were dried, filtered and concentrated. The crude title compound remaining as a residue was purified by column chromatography using toluene/ethanol 95:5 and crystallized from isopropanol. 1.5 g of 2,3-dihydro-5-(4-hydroxyphenyl)- 6-methyl-2-[2-(4-(4-methylpyridin-2-yl)piperazin-1-yl)ethyl] pyrrolo[1,2,3-de]-1,4-benzoxazine were obtained as a white powder having a melting point of 213° to 214° C.

EXAMPLE 3

2,3-Dihydro-5-(4-hydroxyphenyl)-7-methoxy-6-methyl-2-[2-(4-(4-methylpyridin-2-yl)piperazin-1-yl)ethyl] pyrrolo[1,2,3-de]-1,4-benzoxazine A) 6.3 9 of nitric acid were added dropwise at room temperature with stirring to 12.4 g of 4-methoxyphenol in 120 ml of tetrahydrofuran. The reaction mixture was then stirred for half an hour. The solvent was subsequently evaporated and the residue remaining was purified by chromatography using dichloromethane as an eluent. 6.2 g of 2-nitro-4-methoxyphenol were obtained as a yellow powder having a melting point of 72° C.

B) 40 g of 2-nitro-4-methoxyphenol were stirred into a mixture of 200 ml of water and 200 ml of 35% strength sodium hydroxide solution in the dark. 100 g of sodium thiosulfate were added to the reaction mixture and the mixture was stirred at room temperature for a further 2 hours. For work-up, the reaction mixture was neutralized by the addition of 12N hydrochloric acid solution and extracted four times with 500 ml of ethyl acetate. The organic extracts were washed twice with 500 ml of water, dried, filtered and evaporated. 30 g of 2-amino-4-methoxyphenol were obtained as a residue and further processed without further purification.

C) 30 g of 2-amino-4-methoxyphenol were reacted with maleic anhydride according to the method described in Example 1A). 13 g of methyl (6-methoxy-3-oxo-2,3-dihydro- 4H-1,4-benzoxazin-2-yl) acetate were obtained as an oil.

D) 13 g of the ester obtained above were reduced using lithium aluminum hydride in tetrahydrofuran according to the method described in Example 1B). 10.5 g of 4H-2,3-dihydro-2-(2-hydroxyethyl)-6-methoxy-1,4-benzoxazine were obtained as an oil.

E) 10.5 g of the product obtained above were nitrosated according to the method described in Example 1C). 8 g of 2,3-dihydro-2-(2-hydroxyethyl)-6-methoxy-4-nitroso-1,4-benzoxazine were obtained as an oil.

F) 8 g of the nitroso compound obtained above were reduced according to the method described in Example 1D). 4 g of 4-amino-2,3-dihydro-2-(2-hydroxyethyl)-6-methoxy-1,4-benzoxazine were obtained as a sticky compound.

G) 4 g of the hydrazine compound obtained above were reacted with 4-hydroxypropiophenone according to the method described in Example 1E). 2.4 g of 2,3-dihydro-2-(2-hydroxyethyl)-5-(4-hydroxyphenyl)-7-methoxy-6-methylpyrrolo[ 1,2,3-de]-1,4-benzoxazine were obtained as a white solid having a melting point of 190° C.

H) 2.4 g of the alcohol obtained above were converted into the corresponding tosylate according to the method described in Example 1F). 2.3 g of 2,3-dihydro-5-(4-hydroxyphenyl)- 7-methoxy-6-methyl-2-(2-p-toluenesulfonyloxy)ethyl)pyrrolo[ 1,2,3-de]-1,4-benzoxazine were obtained as an oil.

I) 2.3 g of the product obtained above were reacted with 1-[2-(4-methylpyridyl)]piperazine according to the method described in Example 1G). The crude title compound obtained was crystallized from diethyl ether. 0.3 g of the title compound was obtained as a yellow powder having a melting point of 193° to 195° C.

EXAMPLE 4

2,3-Dihydro-7-hydroxy-5-(4-hydroxyphenyl)-6-methyl-2-[2-(4-(4-methylpyridin-2-yl)piperazin-1-yl)ethyl] pyrrolo[1,2,3-de]-1,4-benzoxazine 0.1 g of 2,3-dihydro-5-(4-hydroxyphenyl)-7-methoxy-6-methyl- 2-[2-(4-(4-methylpyridin-2-yl)piperazin-1-yl)ethyl] pyrrolo[1,2,3-de]-1,4-benzoxazine (preparation according to Example 3) was demethylated by treatment with boron

EXAMPLE 5

2,3-Dihydro-5-(4-methoxyphenyl)-6-methyl-2-[4-(4-methylpyridin-2-yl)piperazin-1-ylmethyl]pyrrolo[1,2,3-de] -1,4-benzoxazine A) 68 g of 2-aminophenol were added to a mixture of 430 g of potassium carbonate and 1 l of dimethyl-formamide. The reaction mixture was stirred for half an hour at room temperature. 208 g of ethyl 2,3-dibromopropionate were then added dropwise and the reaction mixture was subsequently stirred for a further 12 hours at a temperature of 45° C. For work-up, the reaction mixture was filtered and the filtrate was poured into 2 liters of water. The mixture was extracted three times with 800 ml of ethyl acetate, and the organic extracts were dried, filtered and evaporated. 110 g of ethyl 4H-2,3-dihydro- 1,4-benzoxazine-2-carboxylate were obtained as an oil.

B) 100 g of the ester obtained above were reduced using lithium aluminum hydride in tetrahydrofuran analogously to the method described in Example 1B). 56 g of 4H-2,3-dihydro-2-hydroxymethyl-1,4-benzoxazine were obtained as an oil.

C) 56 g of the product obtained above were nitrosated according to the method described in Example 1C). 40 g of 2,3-dihydro-2-hydroxymethyl-4-nitroso-1,4-benzoxazine were obtained as an oil.

D) 40 g of the nitroso compound obtained above were reduced using lithium aluminum hydride in tetrahydrofuran according to the method described in Example 1D). 24.5 g of 4-amino-2,3-dihydro-2-hydroxymethyl- 1,4-benzoxazine were obtained as a sticky compound.

E) 24.5 g of the hydrazine compound obtained above were reacted with 4-methoxypropiophenone according to the method described in Example 1E). 34 g of 2,3-dihydro-2-hydroxymethyl-5-(4-methoxyphenyl)-6-methylpyrrolo[ 1,2,3-de]-1,4-benzoxazine were obtained as an oil.

F) 34 g of the alcohol obtained above were converted into the corresponding tosylate according to the method described in Example 1F). 50 g of 2,3-dihydro-5-(4-methoxyphenyl)- 6-methyl-2-(p-toluenesulfonyloxymethyl)pyrrolo[ 1,2,3-de]-1,4-benzoxazine were obtained as an oil.

G) 12 g of the tosylate compound obtained above were reacted with 1-(4-methylpyridin-2-yl)piperazine according to the method described in Example 1G). 5 g of the title compound were obtained as a white powder having a melting point of 260° C.

EXAMPLE 6

2,3-Dihydro-5-(4-methoxyphenyl)-6-methyl-2-[3-(4-(4-methylpyridin-2-yl)piperazin-1-yl)-3-oxopropyl]pyrrolo[1,2,3-de]-1,4-benzoxazine A) 13.7 9 of 2,3-dihydro-2-[2-(p-toluenesulfonyloxy)ethyl]-5-(4-methoxyphenyl)-6-methylpyrrolo[1,2,3-de]- 1,4-benzoxazine (preparation see Example 1F)) were dissolved in 50 ml of hot dimethyl sulfoxide under a nitrogen atmosphere. 2.2 g of potassium cyanide were added to the reaction mixture heated at 80° C. and the mixture was stirred for a further 6 hours. For work-up, the reaction mixture was poured into ice-water after cooling. The resulting brown solid was filtered out and dissolved in dichloromethane. The organic solution was washed with water, dried and evaporated. The crude product remaining as a residue was purified by column chromatography using dichloromethane as an eluent. 9.1 g of 2,3-dihydro-2-(2-cyanoethyl)-5-(4-methoxyphenyl)- 6-methyl-pyrrolo[1,2,3-de]-1,4-benzoxazine were obtained as a white solid having a melting point of 113° to 14° C.

B) Gaseous hydrogen chloride was passed into a solution of 1.9 g of the nitrile compound obtained above in 15 ml of ethanol and the reaction mixture was boiled under reflux for 2 hours 3 ml of water were then added and the mixture was heated under reflux for a further 5 hours with stirring. For work-up, 50 ml of water were added to the mixture after cooling to room temperature. The reaction product was extracted with dichloromethane and purified by column chromatography using petroleum ether/diethyl ether 70:30 as the eluent. 2.2 g of ethyl 3-[2,3-dihydro-5-(4-methoxyphenyl)-6-methylpyrrolo[ 1,2,3-de]-1,4-benzoxazin-2-yl]propionate were obtained as a white solid having a melting point of 154° C.

C) A solution of 3.5 g of potassium hydroxide in 2 ml of water were added to a solution of 2.2 g of the ester obtained above in 10 ml of ethanol. The reaction mixture was heated to reflux for 1 hour. The reaction mixture was then cooled to room temperature and diluted with 20 ml of water. The resulting solution was acidified by addition of 10% strength hydrochloric acid solution and extracted with dichloromethane. The organic phase was dried over sodium sulfate and evaporated. 1.6 g of 3-[2,3-dihydro-5-(4-methoxyphenyl)- 6-methylpyrrolo[1,2,3-de]-1,4-benzoxazin- 2-yl]propionic acid were obtained as a white solid.

D) 1.6 g of the acid obtained above were dissolved in 10 ml of anhydrous dichloromethane under a nitrogen atmosphere. 0.73 g of carbonyldiimidazole were added to the solution and the reaction mixture was then stirred for 1 hour at room temperature. 1 g of 1-(4-methylpyrid-2-yl)piperazine was subsequently added and the reaction mixture was heated under reflux for 1 hour. The reaction mixture was then cooled to room temperature and washed with water which was rendered alkaline (pH=12). The organic phase was subsequently dried, filtered and concentrated. The residue remaining was purified by column chromatography (eluent dichloromethane containing amounts of ethanol rising from 1 to 8% by volume). 2 g of 2,3-dihydro-5-(4-methoxyphenyl)- 6-methyl-2-[3-(4-(4-methylpyridin-2-yl)piperazin- 1-yl)-3-oxopropyl]-pyrrolo[1,2,3-de]-1,4-benzoxazine. 0.2 $H_2O$ were obtained as white crystals having a melting point of 82° to 83° C.

EXAMPLE 7

2,3-Dihydro-5-(4-methoxyphenyl)-6-methyl-2-[3-(4-(4-methylpyridin-2-yl)piperazin-1-yl)propyl]pyrrolo[1,2,3-de]-1,4-benzoxazine 1 g of 2,3-dihydro-5-(4-methoxyphenyl)-6-methyl-2-[3-(4-(4-methylpyridin-1-yl)piperazin-1-yl) -3-oxopropyl] pyrrolo[1,2,3-de]-1,4-benzoxazine (prepared according to Example 6)) was dissolved in 15 ml of anhydrous tetrahydrofuran under a nitrogen atmosphere. 12 ml of a 1 molar borane-tetrahydrofuran complex were added to the solution. The reaction mixture was stirred and heated to reflux for 2 hours. 25 ml of a 6N hydrochloric acid solution were then added and the reaction mixture was stirred for 24 hours. The precipitate formed was dissolved in water which was rendered alkaline (pH=12), and the solution was extracted with dichloromethane. The organic extracts were dried and evaporated. The crude product remaining was purified by column chromatography using dichloromethane containing 2% ethanol as an eluent. The purified title compound was poured into 3N isopropanolic hydrochloric acid solution for conversion into its dihydrochloride salt. 0.6 g of 2,3-dihydro-5-(4-methoxyphenyl)- 6-methyl-2-[3-(4-(4-methylpyridin-2-yl)piperazin- 1-yl)propyl]pyrrolo[1,2,3-de]-1,4-benzoxazine. 2HCl.0.7H$_2$O was obtained as yellow crystals having a melting point of 248° to 249° C.

EXAMPLE 8

2,3-Dihydro-5-(4-methoxyphenyl)-6-methyl-2-[2-(4-(4-methylpyridin-2-yl)piperazin-1-yl)-2-oxoethyl]pyrrolo[1,2,3-de]-1,4-benzoxazine A) 92 g of methyl (3-oxo-2,3-dihydro-4H-1,4-benzoxazin-2-yl)acetate (preparation see Example 1A)) were suspended in 300 ml of dichloromethane. 430 ml of a 1 molar solution of a borane-tetrahydrofuran complex in tetrahydrofuran were added to the suspension. The reaction mixture was stirred for 48 hours at room temperature. 250 ml of 35% strength hydrochloric acid solution were then added to the reaction mixture and it was stirred for a further 2 hours. The reaction mixture was neutralized by addition of 10% strength ammonia solution and extracted with dichloromethane. The organic extracts were washed with water, dried, filtered and concentrated. The oil remaining as a residue was dissolved in 500 ml of acetone. By addition of isopropanolic hydrochloric acid solution and cooling to +5° C., methyl (2,3-dihydro-4H-1,4-benzoxazin- 2-yl)acetate hydrochloride was precipitated from the solution. 70 g of the hydrochloride were obtained as a crystalline solid.

B) 70 g of the above compound were nitrosated according to the method described in Example 1C). 65 g of methyl (2,3-dihydro-4-nitroso-1,4-benzoxazin-2-yl)acetate were obtained as an oil.

C) A solution of 60 g of the nitroso compound obtained above in 700 ml of acetic acid was added to a suspension of 60 g of zinc in 150 ml of water and the reaction mixture was stirred for 12 hours. It was subsequently evaporated and the residue remaining was dissolved in 1 l of dichloromethane. The organic solution was washed twice with 500 ml of water which was rendered alkaline (pH=9) and subsequently twice with 1 l of neutral water, dried over sodium sulfate, filtered and concentrated. The crude product remaining was purified by column chromatography using dichloromethane containing amounts of methanol rising from 1 to 10% by volume as the eluent. 25 g of methyl (4-amino-2,3-dihydro-1,4-benzoxazin-2-yl)acetate were obtained as an oil.

D) 25 g of the hydrazine compound obtained above were reacted according to the method described in Example 1E) with 4-methoxypropiophenone, methanol being used as the reaction medium. The reaction mixture was worked up as described in Example 1E). 10 g of methyl (2,3-dihydro- 5-(4-methoxyphenyl)-6-methyl-pyrrolo[1,2,3-de]- 1,4-benzoxazin-2-yl)acetate were obtained as an oil.

E) 10 g of the ester obtained above were hydrolyzed according to the method described in Example 6C). The acid obtained was purified by column chromatography using ethyl actetate containing amounts of methanol rising from 0 to 10% by volume as the eluent. 3.2 g of (2,3-dihydro-5-(4-methoxypheny)-6-methylpyrrolo[ 1,2,3-de]-1,4-benzoxazin-2-yl)acetic acid were obtained as a sticky residue.

F) 3.2 g of the acid obtained above were reacted with 3 g of 1-(4-methylpyridin-2-yl)]piperazine according to the method described in Example 6D). The crude title compound obtained was purified by column chromatography using ethyl acetate containing amounts of methanol rising from 0 to 10% by volume. 1.7 g of the title compound were obtained as an oil. NMR spectrum (60 MHz, s=singlet, d=doublet, m= multiplet, br=broad): 7.9 ppm (d, 1H), 7.4–6.1 ppm (m, 9H), 4.7 ppm (br s, 3H), 3.8 ppm (s, 3H), 3.6–3 ppm (m, 8H), 2.7–2.5 ppm (m, 2H), 2.3–2 ppm (2s, 6H).

EXAMPLE 9

2,3-Dihydro-5-(3,5-dimethyl-4-hydroxyphenyl)-6-methyl-2-[4-(4-(4-methylpyridin-2-yl)piperazin-1-yl)-4-oxobutyl]-pyrrolo[1,2,3-de]-1,4-benzoxazine A) A mixture of 15.4 g of 2-nitrophenol, 31 g of dimethyl 2-bromoadipate (prepared by bromination of methyl adipate with N-bromosuccinimide in tetrachloromethane in the presence of benzoyl peroxide according to the method described in J. Org. Chem. 18 (1953) 649 to 652) and 46 g of potassium carbonate in 100 ml of dimethyformamide was heated at 40° C. for 4 hours with stirring. For work-up, the reaction mixture was filtered, the filtrate was poured into 200 ml of water and the reaction product was extracted three times with 100 ml portions of ethyl acetate and purified by column chromatography using dichloromethane as the eluent. 28 g of methyl 2-(2-nitrophenoxy)adipate were obtained as an oil.

B) A solution of 13.5 g of the product obtained above in 300 ml of methanol was mixed with 0.7 g of a palladium/carbon catalyst (10% palladium on carbon). Hydrogenation was then carried out for 5 hours at room temperature using a hydrogen pressure of 4 bars. The catalyst was subsequently filtered off from the reaction mixture and the filtrate was evaporated. 9 g of methyl 4-(3-oxo-2,3-dihydro-4H-1,4-benzoxazin-2-yl)butyrate were obtained as an oil.

C) 11.5 g of the product obtained above were reduced using a borane-tetrahydrofuran complex according to the method described in Example 8A). 5 g of methyl 4-(2,3-dihydro- 4H-1,4-benzoxazin-2-yl) butyrate were obtained as an oil.

D) 5 g of the product obtained above were nitrosated by reaction with sodium nitrite according to the method described in Example 1C). 5 g of methyl 4-(2,3-dihydro-4-nitroso-1,4-benzoxazin-2-yl)butyrate were obtained as an oil.

E) 5 g of the nitroso product obtained above were reduced using zinc/acetic acid according to the method described in Example 8C). 4.5 g of methyl 4-(4-amino- 2,3-dihydro-1,4-benzoxazin-2-yl)butyrate were obtained as a sticky compound.

F) 4.5 g of the product obtained above were reacted with (3,5-dimethyl-4-hydroxy) propiophenone (prepared according to the method described in Bull. Soc. Chim. Fra., 1977, 901 to 905 by R. Martin by reaction of 2,6-dimethylphenol with propionyl chloride in dichloromethane in the presence of triethylamine and subsequent treatment of the 2,6-dimethylphenol propionic acid ester formed with aluminum trichloride in nitromethane) according to the method described in Example 1E). 5.2 g of methyl 4-[2,3-dihydro-5-(3,5-dimethyl- 4-hydroxyphenyl)-6-methyl-pyrrolo[1,2,3-de]- 1,4-benzoxazin-2-yl]butyrate were obtained as an oil.

G) 5.2 g of the ester obtained above were hydrolyzed according to the method described in Example 6C). 2 g of 4-[2,3-dihydro-5-(3,5-dimethyl-4-hydroxyphenyl)-6-methylpyrrolo[ 1,2,3-de]-1,4-benzoxazin-2-yl]butyric acid were obtained as a sticky product.

H) 2 g of the acid obtained above were reacted with 1-(4-methylpyridin- 2-yl)piperazine in dichloromethane in the presence of carbonyldiimidazole according to the method described in Example 6D). 0.8 g of the title compound was obtained as white crystals having a melting point of 112° C.

EXAMPLE 10

2,3-Dihydro-5-(4-methoxyphenyl)-2-[2-(4-(4-methylpyridin-2-yl)piperazin-1-yl)ethyl]pyrrolo[1,2,3-de]-1,4-benzoxazine A) A solution of 7.2 g of methoxybenzene in 120 ml of dichloromethane was cooled to 0° C. in an ice-bath. 22 g of aluminum trichloride were then slowly added. The color of the solution changed during the course of this from yellow to pink. 10 g of ethyl malonyl chloride were subsequently added, the color of the solution changing from pink to brown. The reaction mixture was heated under reflux for half an hour and then poured into an ice/water mixture and extracted with dichloromethane. The organic extracts were washed with water, dried, filtered and evaporated. 4.5 g of ethyl 3-(4-methoxyphenyl)-3-oxopropionate were obtained as an oil.

B) 9 g of the ester obtained above were reacted with 8 g of 4-amino-2,3-dihydro-2-(2-hydroxyethyl)-1,4-benzoxazine (preparation see Example 1D)) according to the method described in Example 1E). The crude product obtained was purified by column chromatography using dichloromethane containing 1% ethanol as the eluent. 6 g of ethyl 2,3-dihydro-2-(2-hydroxyethyl-5-(4-methoxyphenyl)pyrrolo[ 1,2,3-de]-1,4-benzoxazine-6-carboxylate were obtained as an oil.

C) 6 g of the compound obtained above were reacted with p-toluenesulfonyl chloride in pyridine according to the method described in Example 1F). 8 g of crude ethyl 2,3-dihydro-5-(4-methoxyphenyl)-2-[2-p-toluenesulfonyloxy)ethyl] pyrrolo[1,2,3-de]-1,4-benzoxazine- 6-carboxylate were obtained as a sticky solid which was further processed without further purification.

D) 8 g of the tosylate obtained above were reacted with 4 g of 1-(4-methylpyridin-2-yl)piperazine in dimethyformamide according to the method described in Example 1G). The reaction product obtained was purified by crystallization from diethyl ether. 1.8 g of ethyl 2,3-dihydro-5-(4-methoxyphenyl)-2-[2-(4-(4-methylpyridin- 2-yl)piperazin-1-yl)ethyl]-pyrrolo[1,2,3-de] -1,4-benzoxazin-6-carboxylate were obtained as a white powder having a melting point of 149° to 150° C.

E) 0.5 g of the ester obtained above was heated under reflux for 3 hours with 0.1 g of potassium hydroxide in 10 ml of ethanol. The solvent was subsequently evaporated and the residue remaining was heated at 170° C. for 8 hours. The residue was then dissolved in 20 ml of ethyl acetate, and the solution was washed twice with 10 ml of water each time and purified by column chromatography. The title compound thus obtained was converted into its dihydrochloride by treatment with 3N isopropanolic hydrochloric acid. 0.3 g of 2,3-dihydro-5-(4-methoxyphenyl)-2-[2-(4-(4-methylpyridin- 2-yl)piperazin-1-yl)ethyl]pyrrolo[1,2,3 -de] -1,4-benzoxazine. 2HCl.1.5H$_2$O was obtained as a brown powder having a melting point of 200° C. (decomposition).

EXAMPLE 11

2,3-Dihydro-5-(3,5-dimethyl-4-hydroxyphenyl)-6-methyl-2-[3-(4-(4-methylpyridin-2-yl)piperazin-1-yl)propyl]-1,4-benzoxazine A) 24 g of 2-aminophenol, 55 g of methyl 2,5-dibromovalerate and 30 g of potassium carbonate were heated to reflux for 5 hours in 250 ml of acetone. For work-up, the reaction mixture was diluted with 250 ml of diethyl ether, washed with 200 ml of water and acidified to pH= 1 using 12N hydrochloric acid solution. The organic phase was separated, washed twice with 100 ml of water each time, dried and evaporated. The residue was crystallized from methanol. 11 g of 2-(3-bromopropyl)- 2H-1,4-benzoxazin-3(4H)one were obtained.

B) 8.5 g of the product obtained above were heated to reflux for 1 hour with 5.6 g of 1-(4-methylpyridin-2-yl)piperazine and 3.5 g of triethylamine in 80 ml of toluene. For work-up the reaction mixture was washed twice with 50 ml of water and concentrated. The residue remaining was purified by column chromatography using ethyl acetate as the eluent. 10 g of 2-[3-(4-(4-methylpyridin- 2-yl)piperazin-1-yl)-propyl]-2H-1,4-benzoxazin- 3(4H)one were obtained as a sticky compound.

C) 10 g of the compound obtained above were reduced using lithium aluminum hydride in tetrahydrofuran according to the method described in Example 1B). 9 g of 4H-2,3-dihydro- 2-[3-(4-(4-methylpyridin-2-yl)piperazin-1-yl)propyl] -1,4-benzoxazine were obtained as an oil.

D) 9 g of the compound obtained above were nitrosated by reaction with sodium nitrite according to the method described in Example 1C). 8 g of 2,3-dihydro-2-[3-(4-(4-methylpyridin-2-yl)piperazin-1-yl)propyl]-4-nitroso-1,4-benzoxazine were obtained as an oil.

E) 8 g of the nitroso compound obtained above were reduced using lithium aluminum hydride in tetrahydrofuran according to the method described in Example 1D). 6 g of 4-amino-2,3-dihydro-2-[3-(4-(4-methylpyridin-2-yl)piperazin- 1-yl)propyl]-1,4-benzoxazine were obtained.

F) 6 g of the product obtained above and 3 g of (3,5-dimethyl- 4-hydroxy)-4-propiophenone were dissolved in 60 ml of ethanol. The reaction mixture was heated to reflux for 2.5 hours under a nitrogen atmosphere. 10 ml of 12N hydrochloric acid solution were then added dropwise at the same temperature distributed over a period of 1 hour. For work-up, the reaction mixture was diluted with water and extracted with dichloromethane. The organic phase was dried over sodium sulfate, filtered and concentrated. The crude product obtained was crystallized from a mixture of diethyl ether/n-hexane 1:1. 5 g of the title compound were obtained as a white powder having a melting point of 110° C.

The compounds of the Formula I shown in the following Table 1 can also be prepared by the processes described in the above examples.

TABLE 1

| Ex. No. | R¹ | R² | R³ | R⁴ | R⁵ | R⁶ | y | n | Z | Q | R⁷ | Salt form (H₂O content in mol/mol) | M.p. in °C. |
|---|---|---|---|---|---|---|---|---|---|---|---|---|---|
| 12 | $CH_3$ | H | H | $CH_3O$ | H | H | O | 2 | bo | N | 4-$CH_3$-pyrid-2- | BA (0.6) | 88–89 |
| 13 | $CH_3$ | H | H | HO | H | H | O | 2 | bo | N | 4-$CH_3$-pyrid-2- | BA (0.7) | 253–254 |
| 14 | $CH_3$ | H | H | H | H | H | O | 1 | bo | N | 4-$CH_3$-pyrid-2- | 2.3 HCl (2) | 218–220 |
| 15 | $CH_3$ | H | H | H | H | H | O | 2 | CO | N | 4-$CH_3$-pyrid-2- | BA (3.1) | 152–153 |
| 16 | $CH_3$ | H | H | H | H | H | O | 2 | $CH_2$ | N | 4-$CH_3$-pyrid-2- | BA (0.7) | 200–201 |
| 17 | $CH_3$ | H | H | H | H | H | O | 1 | CO | N | 4-$CH_3$-pyrid-2- | BA | 150 (D) |
| 18 | $CH_3$ | H | H | $CH_3$ | $CH_3$ | H | O | 3 | $CH_2$ | N | 4-$CH_3$-pyrid-2- | BA (0.6) | 70–71 |
| 19 | $CH_3$ | 7-Cl | H | H | H | H | O | 2 | bo | N | 4-$CH_3$-pyrid-2- | 2 HCl (1.5) | 220 (D) |
| 20 | $CH_3$ | H | H | $CH_3$ | $CH_3$ | H | O | 2 | bo | N | 4-$CH_3$-pyrid-2- | 2 HCl (2.5) | 190–192 |
| 21 | $CH_3$ | H | H | H | H | H | S | 2 | bo | N | 4-$CH_3$-pyrid-2- | 2 HCl (3) | 204–206 |
| 22 | $CH_3$ | 7-F | H | H | H | H | O | 2 | bo | N | 4-$CH_3$-pyrid-2- | BA (0.6) | 128–130 |
| 23 | $CH_3$ | H | H | $CH_3$ | $CH_3$ | H | O | 3 | CO | N | pyrid-2- | BA | 208 |
| 24 | $CH_3$ | H | H | H | H | H | O | 2 | bo | N | 4-F-phen- | HCl (3) | 171–173 |
| 25 | $CH_3$ | H | H | $CH_3$ | $CH_3$ | H | O | 2 | CO | N | 4-$CH_3$-pyrid-2- | BA | 184–185 |
| 26 | $CH_3$ | H | H | $CH_3$ | $CH_3$ | H | O | 2 | CO | N | pyrid-2- | HCl (1) | 180–182 |
| 27 | $CH_3$ | 7-F | H | $CH_3$ | $CH_3$ | H | O | 2 | bo | N | pyrid-2- | 2 HCl (2.2) | 225 (D) |
| 28 | $CH_3$ | 7-F | H | $CH_3$ | $CH_3$ | H | O | 2 | bo | N | 4-$CH_3$-pyrid-2- | 2.3 HCl (5) | 225 (D) |
| 29 | $CH_3$ | 7-F | H | $CH_3$ | $CH_3$ | H | O | 2 | $CH_2$ | N | 4-$CH_3$-pyrid-2- | 2 HCl (3) | 267–269 |
| 30 | $CH_3$ | H | H | H | H | H | O | 1 | $CH_2$ | N | pyrid-2- | 2 BA (0.2) | 199–201 |
| 31 | $CH_3$ | H | H | H | H | H | O | 2 | bo | N | 5-$CH_3$-pyrid-2- | BA (0.5) | 217–220 |
| 32 | $CH_3$ | H | H | H | H | H | O | 2 | bo | N | 3-$CH_3$-pyrid-2- | BA (0.2) | 189–191 |
| 33 | $CH_3$ | H | H | H | H | H | O | 2 | bo | N | 6-$CH_3$-pyrid-2- | BA (1.1) | 176–178 |
| 34 | $CH_3$ | H | H | H | H | H | O | 2 | CO | N | 5-$CH_3$-pyrid-2- | HCl (3) | 243–245 |
| 35 | $CH_3$ | H | H | H | $CH_3O$ | H | O | 2 | bo | N | 3-$CH_3$-pyrid-2- | 2.5 HCl (3.7) | 230–231 |
| 36 | $CH_3$ | H | H | H | H | H | O | 2 | CO | N | pyrid-2- | BA (1.5) | 120–122 |
| 37 | $CH_3$ | H | H | H | H | H | O | 2 | CO | N | 3-$CH_3$-pyrid-2- | BA (0.2) | 112–114 |
| 38 | $CH_3$ | H | H | H | $CH_3O$ | H | O | 2 | CO | N | 4-$CH_3$-pyrid-2- | BA | 114–116 |
| 39 | $CH_3$ | H | H | H | $CH_3O$ | H | O | 2 | CO | N | 5-$CH_3$-pyrid-2- | BA (1.1) | 95–97 |
| 40 | $CH_3$ | H | H | $CH_3$ | $CH_3$ | H | O | 1 | $CH_2$ | CH | opyrim-N—<br>\|<br>$CH_3$ | BA (1) | 255–257 |
| 41 | $CH_3$ | H | H | H | H | H | O | 2 | $CH_2$ | N | 3-$CH_3$-pyrid-2- | BA | 116–118 |
| 42 | $CH_3$ | 8-F | H | $CH_3$ | $CH_3$ | H | O | 2 | bo | N | 4-$CH_3$-pyrid-2- | BA | 108 |
| 43 | $CH_3$ | 8-$CH_3O$ | H | $CH_3$ | $CH_3$ | H | O | 2 | bo | N | 4-$CH_3$-pyrid-2- | BA | 100 |
| 44 | $CH_3$ | 8-HO | H | $CH_3$ | $CH_3$ | H | O | 2 | bo | N | 4-$CH_3$-pyrid-2- | BA (1.1) | 195 |
| 45 | $CH_3$ | 7-Cl | H | H | H | $CH_3$ | O | 2 | bo | N | 4-$CH_3$-pyrid-2- | BA | 178 |
| 46 | $CH_3$ | 7-Cl | H | $CH_3$ | $CH_3$ | $CH_3$ | O | 2 | bo | N | 4-$CH_3$-pyrid-2- | 2.5 HCl (4) | 250 (D) |
| 47 | $CH_3$ | H | H | $CH_3$ | $CH_3$ | $CH_3$ | O | 2 | bo | N | 4-$CH_3$-pyrid-2- | 2 HCl (3) | 169 |
| 48 | $CH_3$ | 7-Cl | H | $CH_3$ | $CH_3$ | H | O | 2 | bo | N | 4-$CH_3$-pyrid-2- | 2 HCl (1) | 250 (D) |
| 49 | $CH_3$ | H | H | HO | H | H | O | 2 | CO | N | 4-$CH_3$-pyrid-2- | BA (1.7) | 120 |
| 50 | $CH_3$ | H | H | H | H | $CH_3$ | S | 2 | bo | N | 4-$CH_3$-pyrid-2- | 2 HCl (2.5) | 195 |
| 51 | $CH_3$ | 7-F | H | H | H | $CH_3$ | O | 2 | bo | N | 4-$CH_3$-pyrid-2- | 2 HCl (3) | 275 (D) |
| 52 | $CH_3$ | H | H | HO | H | $CH_3$ | O | 2 | bo | N | 4-$CH_3$-pyrid-2- | BA | 121–122 |
| 53 | $CH_3$ | H | H | H | H | $CH_3$ | O | 2 | bo | N | 4-F-phen- | HCl (2) | 210–214 |
| 54 | $CH_3$ | 7-F | H | $CH_3$ | $CH_3$ | H | O | 2 | CO | N | 4-$CH_3$-pyrid-2- | BA (1.5) | 168–170 |
| 55 | $CH_3$ | H | H | H | H | H | O | 2 | $CH_2$ | N | 5-$CH_3$-pyrid-2- | 2 HCl (2.1) | 247–249 |
| 56 | $CH_3$ | H | H | H | H | H | O | 2 | $CH_2$ | N | pyrid-2- | 2 HCl (2.4) | 257–260 |
| 57 | $CH_3$ | H | H | H | H | H | O | 2 | CO | N | 6-$CH_3$-pyrid-2- | 1.1 HCl (2.8) | 237–240 |
| 58 | $CH_3$ | H | H | H | H | H | O | 3 | bo | N | 6-$CH_3$-pyrid-2- | 2.2 HCl (3) | 257–259 |
| 59 | $CH_3$ | H | H | $CH_3$ | $CH_3$ | H | O | 2 | bo | N | pyrid-2- | 2 HCl (2.5) | 140 (D) |
| 60 | $CH_3$ | H | H | $CH_3$ | $CH_3$ | H | O | 2 | bo | N | 3-$CH_3$-pyrid-2- | 2 HCl (2) | 170 (D) |
| 61 | $CH_3$ | H | H | $CH_3$ | $CH_3$ | H | O | 2 | bo | N | 6-$CH_3$-pyrid-2- | 2 HCl (2.2) | 140 (D) |
| 62 | $CH_3$ | H | H | $CH_3$ | $CH_3$ | H | O | 2 | bo | N | 5-$CH_3$-pyrid-2- | 2 HCl (2.8) | 100 (D) |
| 63 | $CH_3$ | H | H | $CH_3$ | $CH_3$ | H | S | 3 | $CH_2$ | N | 4-$CH_3$-pyrid-2- | BA | 84–85 |
| 64 | $CH_3$ | H | H | $OCH_3$ | $CH_3$ | H | S | 3 | $CH_2$ | N | 4-$CH_3$-pyrid-2- | BA | 85–86 |
| 65 | $CH_3$ | H | H | $CH_3$ | $CH_3$ | H | O | 3 | $CH_2$ | N | pyrid-2- | BA (1) | 72–73 |
| 66 | $CH_3$ | 7-Cl | 9-$CH_3$ | H | H | H | O | 2 | bo | N | 4-$CH_3$-pyrid-2- | BA | 251 |
| 67 | $CH_3$ | 7-OH | H | $CH_3$ | $CH_3$ | H | O | 2 | CO | N | 4-$CH_3$-pyrid-2- | BA | 204–206 |
| 68 | $CH_3$ | 7-$OCH_3$ | H | H | H | H | O | 2 | CO | N | 4-$CH_3$-pyrid-2- | BA (0.6) | 129–133 |
| 69 | $CH_3$ | 7-OH | H | H | H | H | O | 2 | CO | N | 4-$CH_3$-pyrid-2- | BA (1.5) | 148–150 |
| 70 | $CH_3$ | 7-$CH_3$ | 9-$CH_3$ | H | H | H | O | 2 | bo | N | 4-$CH_3$-pyrid-2- | BA (2.2) | 174–176 |
| 71 | $CH_3$ | 7-OH | H | $CH_3$ | $CH_3$ | H | O | 2 | CO | N | pyrid-2- | BA (1.4) | 130–132 |
| 72 | $CH_3$ | 7-OH | H | $OCH_3$ | $CH_3$ | H | O | 2 | CO | N | pyrid-2- | BA (0.5) | 135 |
| 73 | $CH_3$ | 7-OH | H | $CH_3$ | $CH_3$ | H | O | 3 | bo | N | 4-$CH_3$-pyrid-2- | BA (0.7) | 117–119 |
| 74 | $CH_3$ | 7-OH | H | $CH_3$ | $CH_3$ | H | O | 3 | bo | N | 3-$CH_3$-pyrid-2- | BA (1.1) | 118–120 |
| 75 | $CH_3$ | 7-$OCH_2$<br>\|<br>phen | H | $CH_3$ | $CH_3$ | H | O | 2 | CO | N | pyrid-2- | BA (0.3) | 107–108 | pyrid-2- = pyridin-2-yl

TABLE 1-continued

| Ex. No. | R¹ | R² | R³ | R⁴ | R⁵ | R⁶ | y | n | Z | Q | R⁷ | Salt form (H₂O content in mol/mol) | M.p. in °C. |
|---|---|---|---|---|---|---|---|---|---|---|---|---|---| bo = bond
phen = phenyl
opyrim = 4-oxo-3H-pyrimidin-2-yl
BA = base
HCl = hydrochloride
D = decomposition

Example I

Tablets containing
2,3-dihydro-5-(4-hydroxyphenyl)-
6-methyl-2-[2-(4-(4-methylpyridin-2-yl)piperazin-
1-yl)ethyl]pyrrolo[1,2,3-de]-1,4-benzoxazine Tablets were prepared having the following composition per tablet:

| | |
|---|---|
| 2,3-dihydro-5-(4-hydroxyphenyl)-6-methyl-2-[2-(4-(4-methylpyridin-2-yl)piperazin-1-yl)ethyl]pyrrolo[1,2,3-de]-1,4-benzoxazine | 20 mg |
| Cornstarch | 60 mg |
| Lactose | 135 mg |
| Gelatine (as 10% strength solution) | 6 mg |

The active compound, the cornstarch and the lactose were thickened using the 10% strength gelatine solution. The paste was comminuted, and the resulting granules were transferred to a suitable metal sheet and dried at 45° C. The dried granules were fed through a comminuting machine and mixed with the following further ingredients in a mixer:

| | |
|---|---|
| Talc | 5 mg |
| Magnesium stearate | 5 mg |
| Cornstarch | 9 mg | and then compressed to produce 240 mg tablets.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

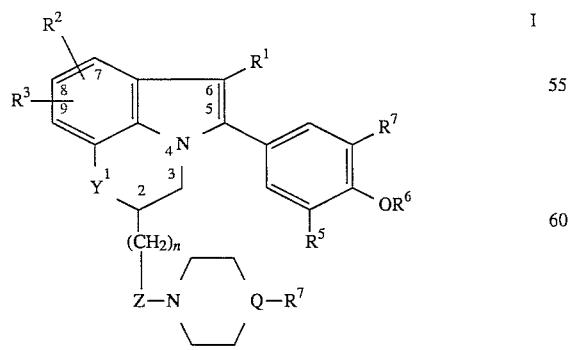

I

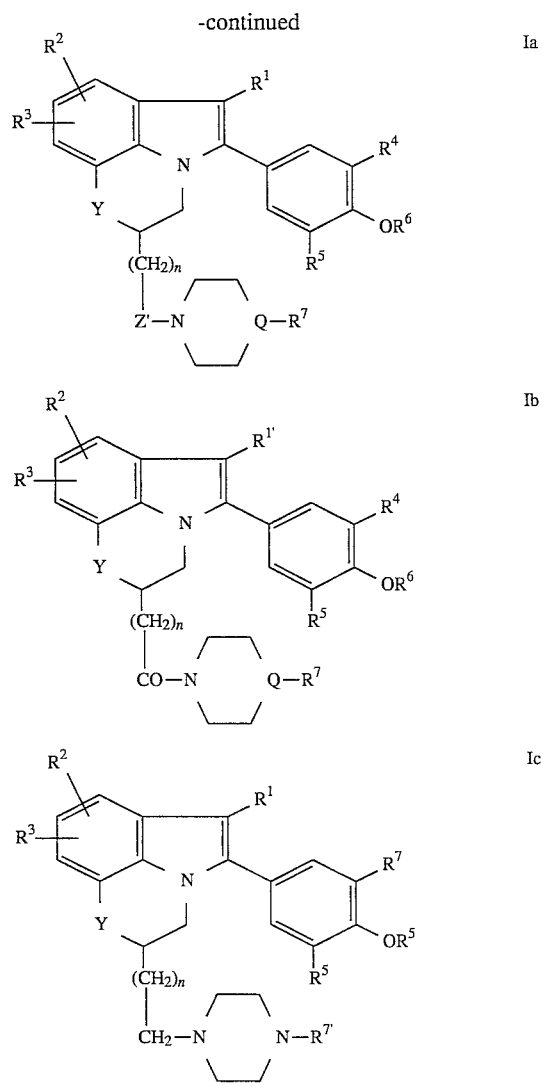

Ia

Ib

Ic

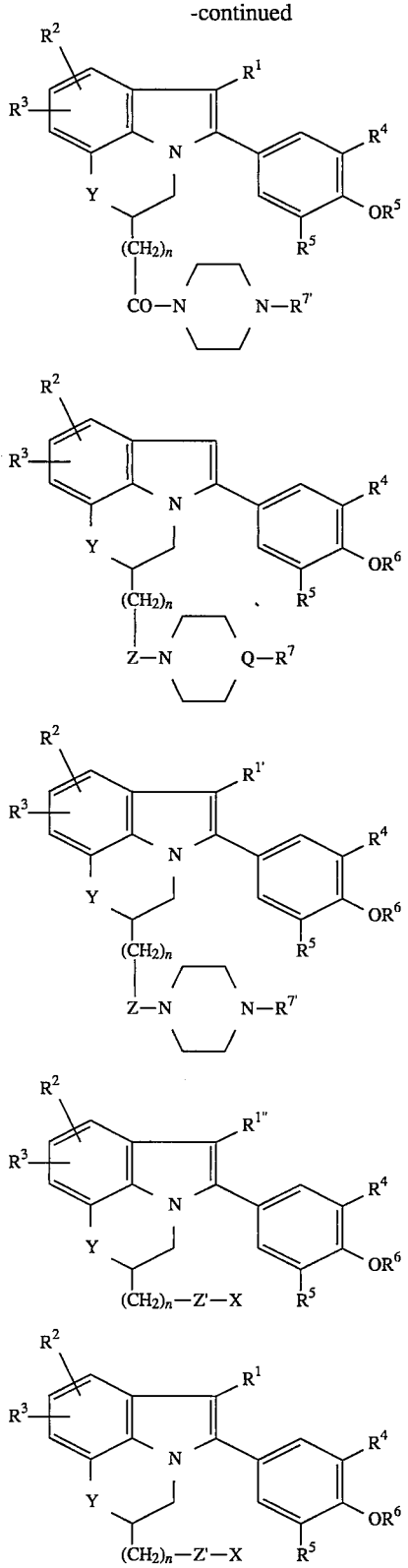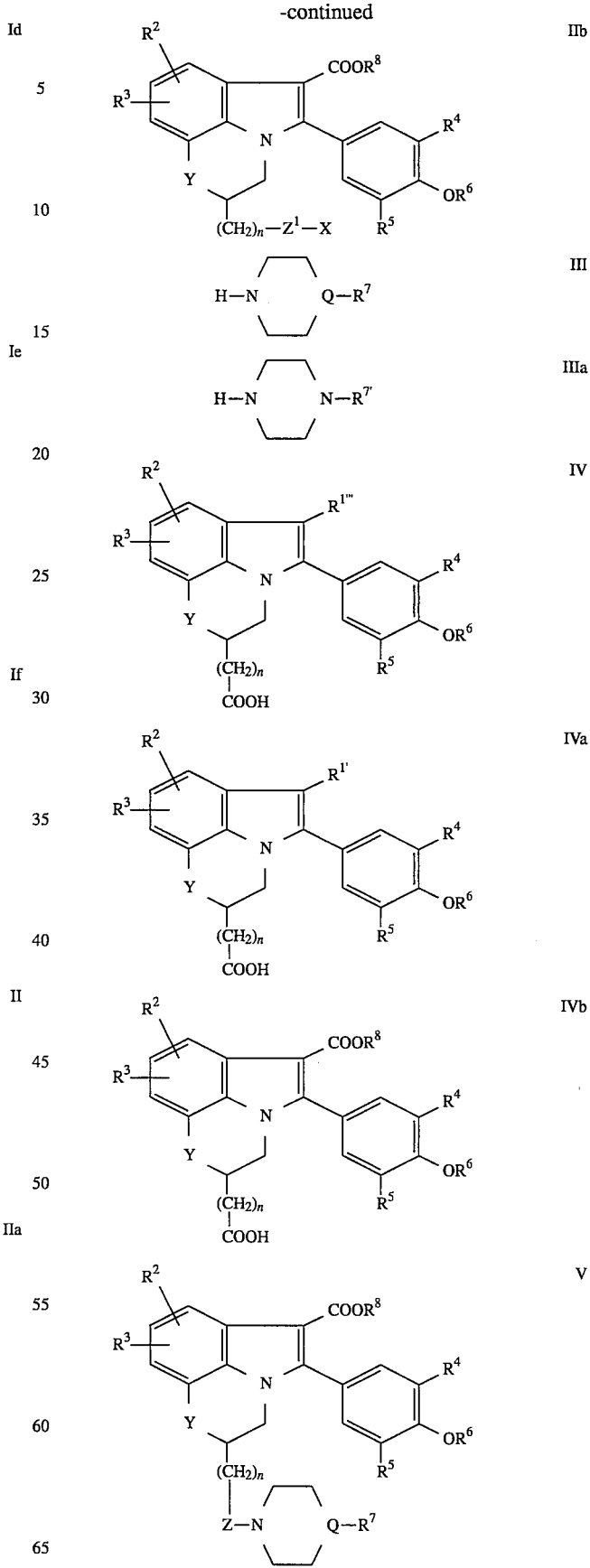

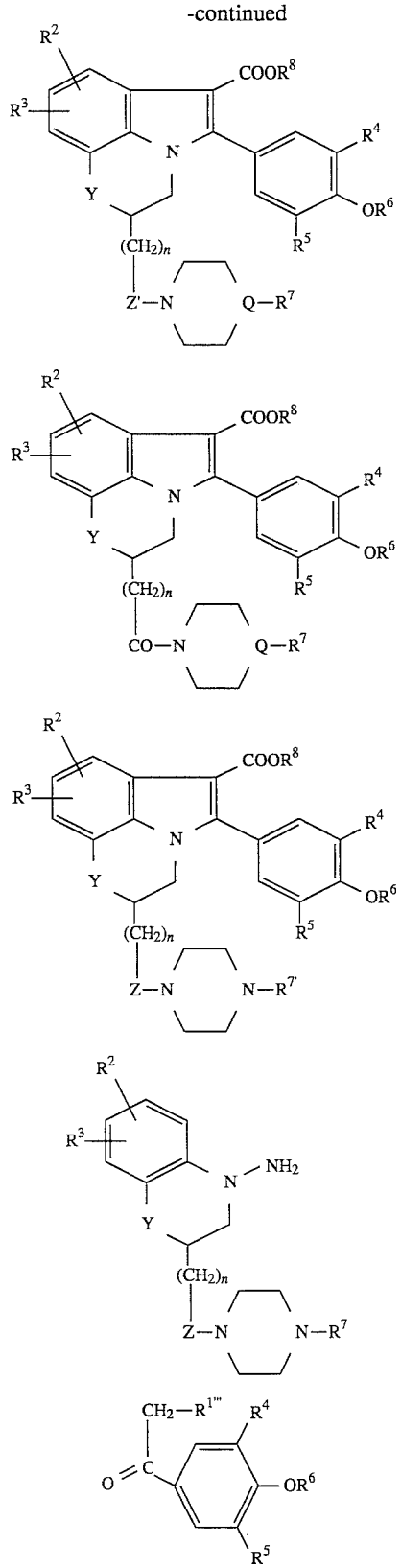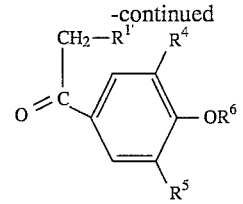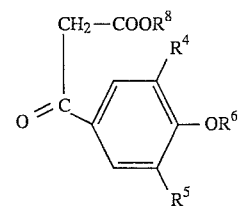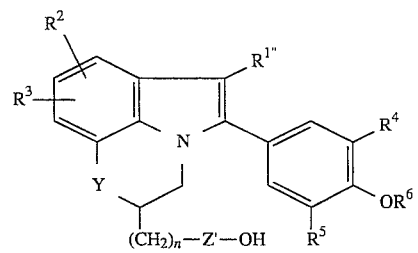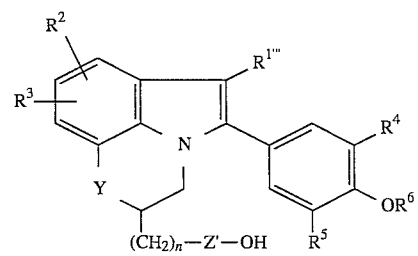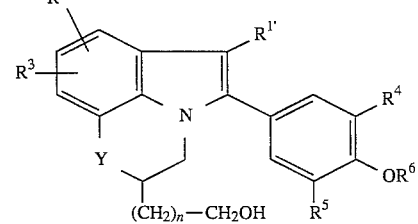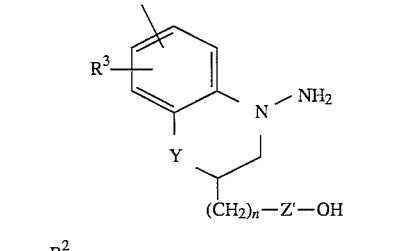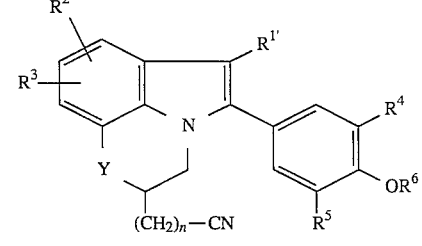

-continued
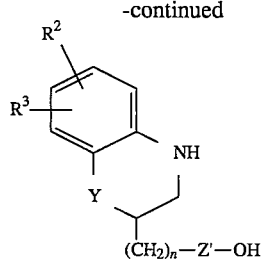 XI
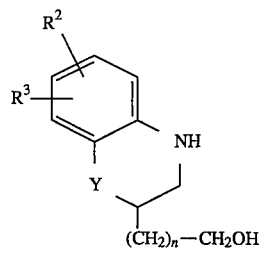 XIa
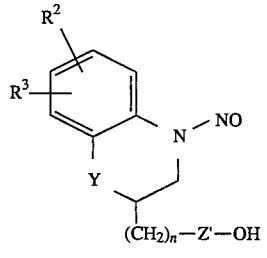 XII
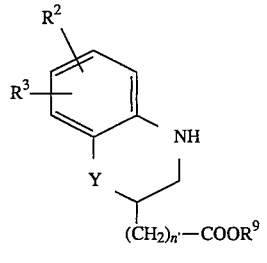 XIII
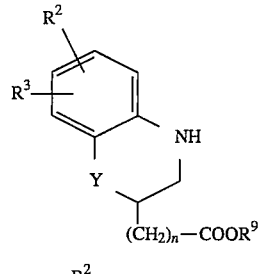 XIIIa
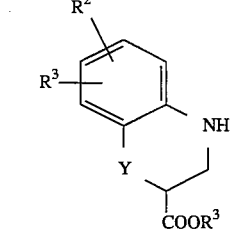 XIIIb
-continued
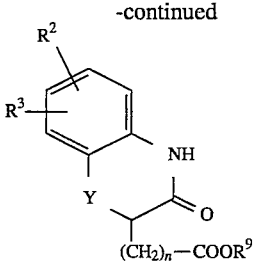 XIV
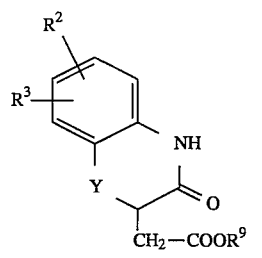 XIVa
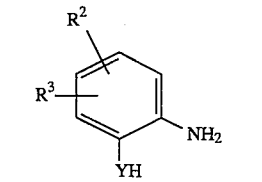 XV
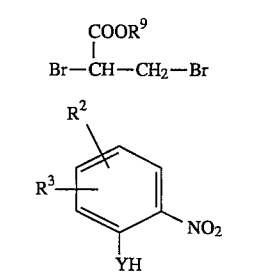 XVI
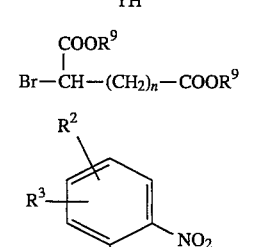 XVII
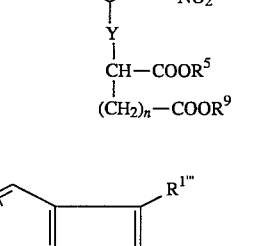 XVIII
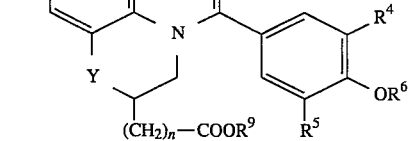 XIX
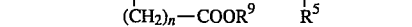 XX -continued
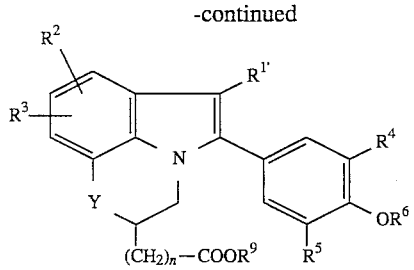
XXa
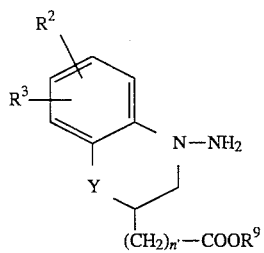
XXI
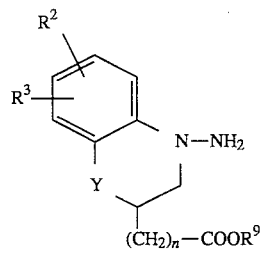
XXIa
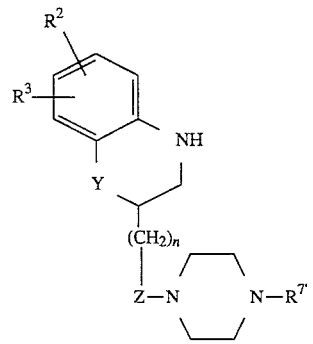
XXII
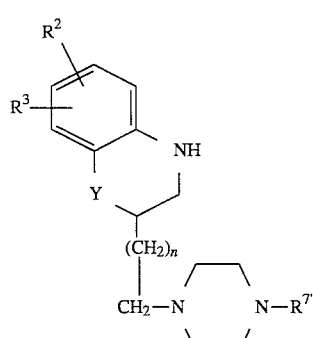
XXIIa
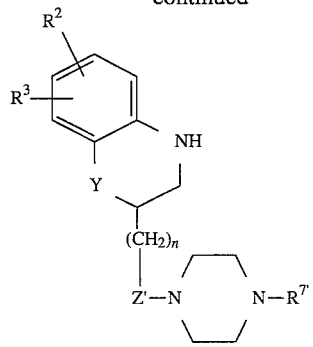
XXIIb
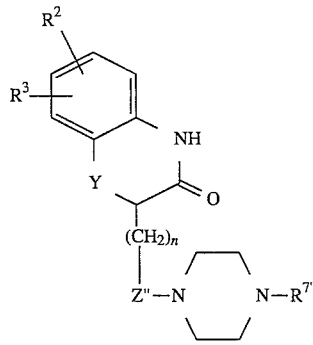
XXIII
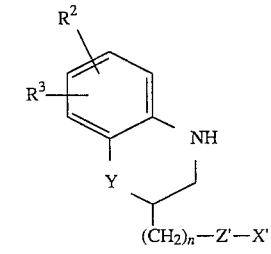
XXIV
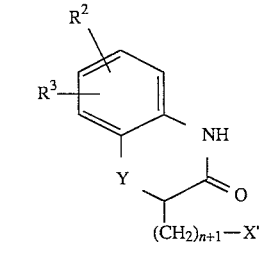
XXV
$$\underset{Br}{\overset{COOR^9}{|}}CH-(CH_2)_{n+1}-X'$$
XXVI
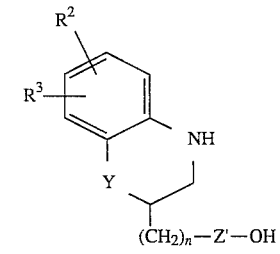
XXVII
$R^{1'''}-CH_2-CO-Cl$
XXVIII -continued

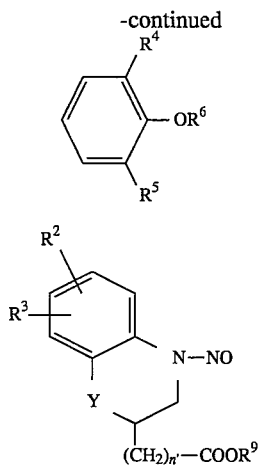

XXIX

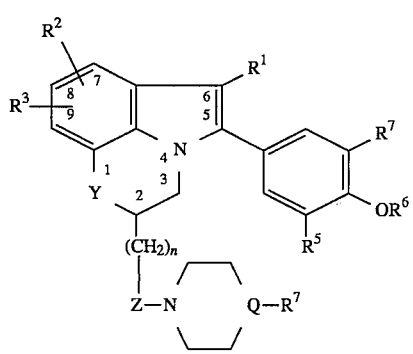

XXX

What is claimed is:

1. A compound corresponding to formula I:

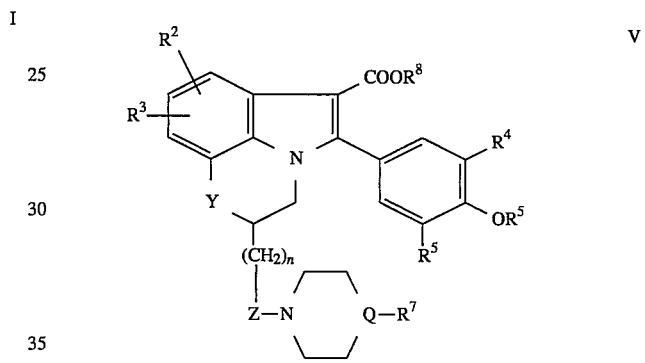

I in which

R$^1$ represents hydrogen or lower alkyl,

R$^2$ represents hydrogen, halogen, lower alkyl, lower alkoxy, benzyloxy or hydroxyl, R$^3$ represents hydrogen, halogen, lower alkyl, lower alkoxy or hydroxyl, R$^4$ represents hydrogen, lower alkyl, lower alkoxy or hydroxyl, R$^5$ represents hydrogen, lower alkyl, lower alkoxy or hydroxyl, R$^6$ represents hydrogen or lower alkyl, Y represents oxygen or sulfur, n represents an integer from 1 to 3, Z represents a bond, a CO group or a CH$_2$ group, Q represents nitrogen or a CH group, and R$^7$, if Q represents nitrogen, represents a pyridyl or phenyl radical which is optionally substituted by lower alkyl or halogen, or, if Q represents a CH group, represents a N-methyl-N-(4-oxo-3H-pyrimidin-2-yl)amino group, or a physiologically acceptable acid addition salt thereof.

2. A compound according to claim 1, wherein R$^2$ represents hydrogen, halogen, lower alkyl, lower alkoxy or hydroxyl.

3. A compound according to claim 1, wherein R$^6$ represents hydrogen.

4. A compound according to claim 1, wherein Y represents oxygen.

5. A compound according to claim 1, wherein R$^1$ represents a lower alkyl group.

6. A compound according to claim 5, wherein R$^1$ represents a methyl group.

7. A compound according to claim 1, wherein Q represents nitrogen, and R$^7$ represents an unsubstituted pyridyl group or a pyridyl group substituted by lower alkyl or halogen.

8. A compound according to claim 7, wherein R$^7$ represents a 4-methylpyrid-2-yl group.

9. A pharmaceutical composition comprising an effective antiinflammatory or antiallergic amount of a compound according to claim 1, and at least one pharmaceutical carrier or adjuvant.

10. A compound corresponding to formula V:

V in which

R$^8$ represents lower alkyl,

R$^2$ represents hydrogen, halogen, lower alkyl, lower alkoxy, benzyloxy or hydroxyl, R$^3$ represents hydrogen, halogen, lower alkyl, lower alkoxy or hydroxyl, R$^4$ represents hydrogen, lower alkyl, lower alkoxy or hydroxyl, R$^5$ represents hydrogen, lower alkyl, lower alkoxy or hydroxyl, R$^6$ represents hydrogen or lower alkyl, represents oxygen or sulfur, Y represents an integer from 1 to 3, n represents a bond, a CO group or a CH$_2$ group, Z represents nitrogen or a CH group, and R$^7$, if Q represents nitrogen, represents a pyridyl or phenyl group or a pyridyl or phenyl group substituted by lower alkyl or halogen, or, if Q represents a CH group, R$^7$ represents a N-methyl-N-( 4-oxo-3H-pyrimidin-2-yl)amino group.

* * * * *